US011857514B2

(12) United States Patent
Abbott et al.

(10) Patent No.: US 11,857,514 B2
(45) Date of Patent: *Jan. 2, 2024

(54) TOPICAL COPPER ION TREATMENTS AND METHODS OF TREATMENT USING TOPICAL COPPER ION TREATMENTS IN THE DERMATOLOGICAL AREAS OF THE BODY

(71) Applicant: CDA Research Group, Inc., Pittsburgh, PA (US)

(72) Inventors: Chunlim Abbott, Pittsburgh, PA (US); Dominic C. Abbott, Pittsburgh, PA (US)

(73) Assignee: CDA RESEARCH GROUP, INC., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,442

(22) Filed: Jul. 24, 2019

(65) Prior Publication Data

US 2019/0343876 A1 Nov. 14, 2019

Related U.S. Application Data

(63) Continuation of application No. 13/842,387, filed on Mar. 15, 2013, now Pat. No. 10,398,733.

(51) Int. Cl.
| | | |
|---|---|---|
| *A61K 33/34* | (2006.01) | |
| *A61L 26/00* | (2006.01) | |
| *A61K 9/00* | (2006.01) | |
| *A61K 9/02* | (2006.01) | |
| *A61K 9/06* | (2006.01) | |
| *A61L 15/44* | (2006.01) | |
| *A61L 17/00* | (2006.01) | |

(52) U.S. Cl.
CPC ............ *A61K 33/34* (2013.01); *A61K 9/0014* (2013.01); *A61K 9/0031* (2013.01); *A61K 9/0034* (2013.01); *A61K 9/02* (2013.01); *A61K 9/06* (2013.01); *A61L 15/44* (2013.01); *A61L 17/005* (2013.01); *A61L 26/0066* (2013.01); *A61L 26/0076* (2013.01); *A61L 2300/102* (2013.01)

(58) Field of Classification Search
CPC ........ A61K 9/0014; A61K 9/06; A61K 33/34; A61K 9/0031; A61K 9/0034; A61K 9/02; A61K 9/0048; A61L 2300/102; A61L 15/44; A61L 26/0066
See application file for complete search history.

(56) References Cited

U.S. PATENT DOCUMENTS

| | | |
|---|---|---|
| 2,994,642 A | 8/1961 | Bossard |
| 3,393,678 A | 7/1968 | Pacini |
| 3,803,308 A | 4/1974 | Zipper |
| 3,814,809 A | 6/1974 | Gordon |
| 3,930,834 A | 1/1976 | Schulteis et al. |
| 3,934,580 A | 1/1976 | Cournut |
| 4,039,406 A | 8/1977 | Stanley et al. |
| 4,136,172 A | 1/1979 | Walliczek |
| 4,242,192 A | 12/1980 | Dunning, Jr. et al. |
| 4,246,896 A | 1/1981 | Horne, Jr. et al. |
| 4,294,894 A | 10/1981 | Vellucci |
| 4,332,791 A | 6/1982 | Raaf et al. |
| 4,391,270 A | 7/1983 | Uragami |
| 4,407,786 A | 10/1983 | Drake et al. |
| 4,457,909 A | 7/1984 | Tames |
| 4,618,489 A | 10/1986 | Pollock et al. |
| 4,642,230 A | 2/1987 | Whitehead et al. |
| 4,661,101 A | 4/1987 | Sustmann |
| 4,675,014 A | 6/1987 | Sustmann et al. |
| 4,680,309 A | 7/1987 | Maurer |
| 4,795,628 A | 1/1989 | Afseth |
| 4,959,216 A | 9/1990 | Daunter |
| 5,037,634 A | 8/1991 | Williams et al. |
| 5,063,065 A | 11/1991 | Bazterrica et al. |
| 5,164,367 A | 11/1992 | Pickart |
| 5,211,940 A | 5/1993 | Ishiguro et al. |
| 5,389,360 A | 2/1995 | Mobley et al. |
| 5,415,866 A | 5/1995 | Zook |
| 5,425,862 A | 6/1995 | Hartmann et al. |

(Continued)

FOREIGN PATENT DOCUMENTS

| | | |
|---|---|---|
| AU | 040296/72 | 9/1973 |
| AU | 2020201265 | 9/2021 |

(Continued)

OTHER PUBLICATIONS

US 11,052,109 B2, 07/2021, Abbott et al. (withdrawn)
US 11,229,598 B2, 01/2022, Abbott et al. (withdrawn)
US 11,266,597 B2, 03/2022, Abbott et al. (withdrawn)
"Assessment of the Safety and Efficacy of 3VM1001 Cream for Treatment of Chronic Pain Caused by Knee Osteoarthritis", ClinicalTrials.gov, https://clinicaltrials.gov/ct2/history/NCT02332148?V_3, dated Aug. 19, 2015 (6 pages).
"Copper Sulfate", extract from Extoxnet: Extension Toxicology Network, <http://pmep.cce.cornell.edu/profiles/extoxnet/carbaryl-dicrotophos/copper-sulfate-ext.html>, May 1994 (2 pages).
"Copper Sulphate's Role in Agriculture", Excerpt from PAN Pesticides Database—Chemicals (1 page).
"Dangers of Copper Compounds (Sulfate, etc.)", Pubchem.ncbi.nlm.nih.gov/compound/Copper_sulfate#section=Top, 2007 (17 pages).

(Continued)

*Primary Examiner* — Johann R Richter
*Assistant Examiner* — Danielle Sullivan
(74) *Attorney, Agent, or Firm* — Wilmer Cutler Pickering Hale and Dorr LLP

(57) ABSTRACT

Copper ion treatments for dermatological areas of the body include solutions, creams, lotions, gels, foams, wound dressings, skin patches and suture material, each containing copper ions that bring about therapeutic effects when the copper ion treatments are applied to dermatological tissue. Methods of treating dermatological areas of the body include treatments for use on the skin and nails to treat conditions including disease, infection, inflammation, damaged or injured tissue, tissue needing to be sutured, rashes and other undesirable dermatological conditions.

16 Claims, 6 Drawing Sheets

(56) References Cited

U.S. PATENT DOCUMENTS

| | | | |
|---|---|---|---|
| 5,456,602 A * | 10/1995 | Sakuma | A61K 6/40 |
| | | | 433/215 |
| 5,458,746 A | 10/1995 | Burgess et al. | |
| 5,631,017 A | 5/1997 | Sharpe et al. | |
| 5,654,341 A | 8/1997 | Struewing | |
| 5,798,116 A | 8/1998 | Brown | |
| 5,981,475 A | 11/1999 | Reynolds | |
| 6,022,545 A | 2/2000 | Schmittmann et al. | |
| 6,042,848 A | 3/2000 | Lawyer et al. | |
| 6,087,549 A | 7/2000 | Flick | |
| 6,123,925 A | 9/2000 | Barry et al. | |
| 6,153,210 A | 11/2000 | Roberts et al. | |
| 6,231,889 B1 | 5/2001 | Richardson et al. | |
| 6,294,186 B1 | 9/2001 | Beerse et al. | |
| 6,296,881 B1 * | 10/2001 | Hata | A61K 33/26 |
| | | | 514/474 |
| 6,319,391 B1 | 11/2001 | Holderness et al. | |
| 6,383,352 B1 | 5/2002 | Shyu et al. | |
| 6,787,160 B2 | 9/2004 | Shacknai | |
| 7,005,556 B1 | 2/2006 | Becker et al. | |
| 7,087,249 B2 | 8/2006 | Burrell et al. | |
| 7,252,839 B2 | 8/2007 | Hallinen et al. | |
| 7,604,819 B2 | 10/2009 | Huey et al. | |
| 7,776,915 B2 | 8/2010 | Morariu | |
| 7,857,961 B2 | 12/2010 | Hayashi et al. | |
| 8,118,028 B2 | 2/2012 | Karpati | |
| 8,135,466 B2 | 3/2012 | Fuller et al. | |
| 8,182,800 B2 | 5/2012 | MacDonald | |
| 10,398,733 B2 | 9/2019 | Abbott et al. | |
| 11,000,545 B2 | 5/2021 | Abbott et al. | |
| 11,007,143 B2 * | 5/2021 | Abbott | A61K 9/006 |
| 11,083,750 B2 * | 8/2021 | Abbott | A61K 9/0034 |
| 11,193,184 B2 | 12/2021 | Abbott et al. | |
| 11,253,544 B2 | 2/2022 | Abbott et al. | |
| 11,298,316 B2 * | 4/2022 | Abbott | A61K 9/0036 |
| 11,318,089 B2 * | 5/2022 | Abbott | A61K 33/34 |
| 11,459,638 B2 | 10/2022 | Abbott et al. | |
| 2002/0114767 A1 | 8/2002 | Rolla | |
| 2002/0136758 A1 | 9/2002 | Jehan | |
| 2003/0099718 A1 | 5/2003 | Burrell et al. | |
| 2003/0163149 A1 | 8/2003 | Heisinger | |
| 2003/0166510 A1 | 9/2003 | Pickart | |
| 2004/0120908 A1 | 6/2004 | Cohen | |
| 2004/0171519 A1 | 9/2004 | DiSpirito et al. | |
| 2004/0182694 A1 | 9/2004 | Nevosi | |
| 2004/0254097 A1 * | 12/2004 | Patt | A61P 17/10 |
| | | | 514/2.4 |
| 2005/0031707 A1 | 2/2005 | Schmidt et al. | |
| 2005/0048007 A1 | 3/2005 | Ruggles | |
| 2005/0123620 A1 | 6/2005 | Chiou | |
| 2005/0169852 A1 | 8/2005 | Roberge et al. | |
| 2005/0226945 A1 | 10/2005 | Ruwart | |
| 2006/0122095 A1 | 6/2006 | Delvin et al. | |
| 2006/0216258 A1 | 9/2006 | Singleton et al. | |
| 2006/0222622 A1 | 10/2006 | Faure | |
| 2006/0253078 A1 | 11/2006 | Wu et al. | |
| 2007/0014839 A1 | 1/2007 | Bracht | |
| 2007/0053849 A1 | 3/2007 | Doyle et al. | |
| 2007/0167971 A1 | 7/2007 | Huey et al. | |
| 2007/0187327 A1 | 8/2007 | George et al. | |
| 2007/0190175 A1 | 8/2007 | Cummins et al. | |
| 2007/0243263 A1 * | 10/2007 | Trogolo | A61L 2/238 |
| | | | 424/604 |
| 2007/0275021 A1 | 11/2007 | Lee et al. | |
| 2007/0275073 A1 | 11/2007 | Huey et al. | |
| 2007/0276308 A1 | 11/2007 | Huey et al. | |
| 2008/0029915 A1 | 2/2008 | Waldron | |
| 2008/0032119 A1 | 2/2008 | Feldhahn et al. | |
| 2008/0081077 A1 | 4/2008 | Faryniarz et al. | |
| 2008/0112988 A1 | 5/2008 | Frank et al. | |
| 2008/0125686 A1 | 5/2008 | Lo | |
| 2008/0193427 A1 | 8/2008 | Kaesler et al. | |
| 2008/0195033 A1 | 8/2008 | Eagleson et al. | |
| 2008/0274065 A1 | 11/2008 | Robinson et al. | |
| 2008/0286180 A1 | 11/2008 | Jones et al. | |
| 2008/0286212 A1 | 11/2008 | Cooley | |
| 2008/0295843 A1 | 12/2008 | Haas | |
| 2008/0299155 A1 | 12/2008 | McCook et al. | |
| 2008/0311165 A1 | 12/2008 | Gabbay | |
| 2008/0311218 A1 | 12/2008 | Oronsky et al. | |
| 2008/0312583 A1 | 12/2008 | Oronsky et al. | |
| 2008/0317836 A1 | 12/2008 | Dorogi et al. | |
| 2009/0004294 A1 * | 1/2009 | Margulies | A61K 33/24 |
| | | | 424/649 |
| 2009/0018213 A1 | 1/2009 | Snyder et al. | |
| 2009/0026083 A1 | 1/2009 | Shinji et al. | |
| 2009/0148540 A1 | 6/2009 | Martin et al. | |
| 2009/0163551 A1 | 6/2009 | Earnest | |
| 2009/0186071 A1 | 7/2009 | Huey et al. | |
| 2009/0246292 A1 | 10/2009 | Seville et al. | |
| 2009/0287131 A1 | 11/2009 | Neron et al. | |
| 2009/0304813 A1 | 12/2009 | Hickok | |
| 2009/0311305 A1 | 12/2009 | Abbott et al. | |
| 2010/0003198 A1 * | 1/2010 | Stolmeier | A61K 49/00 |
| 2010/0015898 A1 | 1/2010 | An et al. | |
| 2010/0055138 A1 | 3/2010 | Margulies et al. | |
| 2010/0068161 A1 | 3/2010 | Todary Michael | |
| 2010/0068297 A1 | 3/2010 | Naughton | |
| 2010/0100188 A1 | 4/2010 | Fuller et al. | |
| 2010/0158989 A1 | 6/2010 | Mentkow et al. | |
| 2010/0228174 A1 | 9/2010 | Huey et al. | |
| 2010/0233248 A1 | 9/2010 | Huey et al. | |
| 2010/0307503 A1 | 12/2010 | Iwamoto et al. | |
| 2011/0064826 A1 | 3/2011 | Spurge | |
| 2011/0086088 A1 | 4/2011 | Berry | |
| 2011/0195108 A1 | 8/2011 | Fujimori et al. | |
| 2012/0063262 A1 | 3/2012 | Imran | |
| 2012/0071807 A1 | 3/2012 | McClure, Jr. | |
| 2012/0071858 A1 | 3/2012 | Abbott et al. | |
| 2012/0089068 A1 | 4/2012 | McClure, Jr. | |
| 2013/0095184 A1 | 4/2013 | Lyczak et al. | |
| 2013/0108670 A1 | 5/2013 | Lynch | |
| 2013/0123716 A1 | 5/2013 | Abbott et al. | |
| 2013/0226061 A1 | 8/2013 | Dickson | |
| 2014/0005116 A1 | 1/2014 | Obayan et al. | |
| 2014/0178313 A1 | 6/2014 | Okumura et al. | |
| 2014/0221948 A1 | 8/2014 | Riesinger | |
| 2014/0271495 A1 | 9/2014 | Abbott et al. | |
| 2014/0271797 A1 | 9/2014 | Abbott et al. | |
| 2014/0271798 A1 | 9/2014 | Abbott et al. | |
| 2014/0271919 A1 | 9/2014 | Abbott et al. | |
| 2016/0008272 A1 | 1/2016 | Abbott et al. | |
| 2017/0000823 A1 | 1/2017 | Abbott et al. | |
| 2017/0101699 A1 | 4/2017 | Moskovchenko et al. | |
| 2018/0071206 A1 | 3/2018 | Abbott et al. | |
| 2018/0133250 A1 | 5/2018 | Abbott et al. | |
| 2019/0343732 A1 | 11/2019 | Mao et al. | |
| 2019/0343876 A1 | 11/2019 | Abbott et al. | |
| 2020/0206264 A1 | 7/2020 | Abbott et al. | |
| 2020/0270723 A1 | 8/2020 | Abbott et al. | |
| 2020/0281972 A1 | 9/2020 | Abbott et al. | |
| 2021/0220397 A1 | 7/2021 | Abbott et al. | |
| 2021/0220398 A1 | 7/2021 | Abbott et al. | |
| 2021/0220399 A1 | 7/2021 | Abbott et al. | |
| 2021/0228476 A1 | 7/2021 | Abbott et al. | |
| 2022/0226235 A1 | 7/2022 | Abbott et al. | |

FOREIGN PATENT DOCUMENTS

| | | |
|---|---|---|
| CA | 2478137 A1 | 2/2006 |
| CA | 2912628 | 9/2014 |
| CA | 3130099 | 8/2020 |
| CN | 101203232 A | 6/2008 |
| CN | 101534823 A | 9/2009 |
| EP | 0115130 B1 | 1/1987 |
| EP | 1236461 A1 | 9/2002 |
| EP | 1627641 A1 | 2/2006 |
| EP | 3003046 B1 | 4/2016 |
| EP | 2762125 B1 | 8/2016 |
| FR | 2751544 A1 | 1/1998 |
| GB | 521215 A | 5/1940 |
| GB | 1333906 A | 10/1973 |
| GB | 1493750 A | 11/1977 |
| GB | 2449893 A | 12/2008 |

(56) References Cited

FOREIGN PATENT DOCUMENTS

| | | |
|---|---|---|
| JP | 3075995 U | 3/2001 |
| JP | 2003212765 A | 7/2003 |
| JP | 2010-265519 A | 11/2010 |
| RU | 2051154 C1 | 12/1995 |
| RU | 2155047 C1 | 8/2000 |
| SU | 1538101 | 1/1990 |
| WO | WO-9215329 A1 | 9/1992 |
| WO | WO-9958095 A2 | 11/1999 |
| WO | WO-2001026665 A1 | 4/2001 |
| WO | WO-0239963 A1 | 5/2002 |
| WO | WO-0241862 A1 | 5/2002 |
| WO | WO-02096202 A1 | 12/2002 |
| WO | WO-2004073758 A1 | 9/2004 |
| WO | WO-2005072691 A1 | 8/2005 |
| WO | WO-2006096937 A1 | 9/2006 |
| WO | WO-2008037262 A1 | 4/2008 |
| WO | WO-2009042402 A2 | 4/2009 |
| WO | WO-2009088270 | 7/2009 |
| WO | WO-2011069184 A1 | 6/2011 |
| WO | WO-2012063262 A2 | 5/2012 |
| WO | WO-2014150716 A1 | 9/2014 |
| WO | WO-2014150719 A1 | 9/2014 |
| WO | WO-2014151350 | 9/2014 |
| WO | WO-2018052995 | 3/2018 |
| WO | WO-2020171994 | 8/2020 |
| WO | WO-2021236231 | 11/2021 |

OTHER PUBLICATIONS

"Lowering Infection Rates in Hospitals and Healthcare Facilities—The Role of Copper Alloys in Battling Infectious Organisms", Copper, BioHealth Partnership Publication, Edition 1, Mar. 2007, 26 pages.
"New Molecular Test Available to Diagnose Trichomonas Vaginalis in Asymptomatic and Symptomatic Females", PR Newswire, Oct. 18, 2012, 3 pages.
"Visual Analogue Scale", https://web.archive.org/web/20150804080655/https://www.physio-pedia.com/Visual_Analogue_Scale, Aug. 4, 2015, accessed Dec. 13, 2017 (6 pages).
"WOMAC Osteoarthritis Index," https://web.archive.org/web/20150907191904/https://www.physio-pedia.com/WOMAC_Osteoarthritis_Index, Sep. 7, 2015, accessed Dec. 13, 2017 (4 pages).
Amazon.com search for "Mouthwash", https://www.amazon.com/s/ref=sr_nr_n_0?fst=p90x%3A1%2Cas%3Aoff&rh=n%3A3760911%2Cn%3A10079992011%2Cn%3A3778161%2Ck%3Amouthwash&keywords=mouthwash&ie=UTF8&qid=1502940655&rnid=11055981, dated Aug. 16, 2017 (11 pages).
Anthoni, J.F., "The Chemical Composition of Sea Water", http://www.seafriends.org.nz/oceano/seawater.htm, accessed Jul. 28, 2016 (10 pages).
ASTM International, Designation: D1688-12, "Standard Test Methods for Copper in Water", dated 2012, accessed Oct. 24, 2018 (10 pages).
Blakley, "Overview of Copper Poisoning", Merck Manual: Veterinary Manual, www.merckvetmanual.com/toxicology/copper-poisoning/overview-of-copper-poisoning, 2018 (3 pages).
Borkow, G et al., "Copper as a Biocidal Tool", Current Medicinal Chemistry, 12:2163-2175 (2005) (13 pages).
Cao, "Man Sperm Self Report", Harbin Publishing House, p. 27, Mar. 2012 (2 pages)—with English Translation.
CDA Research Group, Inc., "Assessment of the Safety and Efficacy of 3VM1001 Cream for Treatment of Chronic Pain Caused by Knee Osteoarthritis", U.S. National Library of Medicine, Clinical Trial NCT02332148, https://clinicaltrials.gov/ct2/show/NCT02332148, Aug. 21, 2015, accessed Dec. 12, 2017 (5 pages).
Centers for Disease Control, "CDC No Longer Recommends Oral Drug for Gonorrhea Treatment", Press Release, Aug. 9, 2012, 1 page.
Centers for Disease Control. "Pelvic Inflammatory Disease (PID)", CDC Fact Sheet, Dec. 12, 2012, 6 pages.
Collins, Reflections of Dentifrice Ingredients, Benefits and Recommendations: A Peer-Reviewed Publication, www.ineedce.com, accessed https://www.dentalacademyofce.com/courses/2086/pdf/1103cei_dentifrices_web.pdf, Oct. 2009 (11 pages).
Copper Gluconate, except from Wikipedia, https://en.wikipedia.org/wiki/Copper_gluconate, Mar. 29, 2017 (1 page).
Copper Glycinate Product Data Sheet, https://www.lookchem.com/Copper-glycinate/, dated 2008, accessed Aug. 30, 2018 (2 pages).
Database WPI, Week 199640, Thompson Scientific, London GB, AN 1996-400647, XP002765918, 1996 (2 pages).
Database WPI, Week 200375, Thompson Scientific, AN 2003-793474, XP002767346, 2003 (2 pages).
Dispose—definition, https://www.merriam-webster.com/dictionary/dispose, downloaded Jun. 24, 2018 (1 page).
Edematous—Definition from The Medical Dictionary of the Free Dictionary Online, https://medical-dictionary.thefreedictionary.com/edematous, accessed Mar. 7, 2018 (7 pages).
European Extended Search Report issued in EP14767396.6, dated Feb. 9, 2017 (10 pages).
European Extended Search Report issued in EP14768757.8, dated Dec. 6, 2016 (9 pages).
European Extended Search Report issued in EP14768896.4, dated Feb. 27, 2017 (8 pages).
Extended European Search Report issued in EP14767738.9, dated Jan. 2, 2017 (8 pages).
Faltermeier, R. B., "The Evaluation of Corrosion Inhibitors for Application to Copper and Copper Alloy Archaeological Artefacts", Thesis Submitted for the Degree of Doctor of Philosophy in the Faculty of Science of the University of London, Department of Conservation and Museum Studies, Institute of Archaeology, University College London, University of London, Jul. 1995 (332 pages).
Gerasimov, V. V. et al., "Effect of Temperature on the Rate of Corrosion of Metals", Russian Chemical Bulleting, pp. 1192-1197, Oct. 6, 1957 (6 pages).
Higdon, J. et al., "Copper", Linus Pauling Institute, Oregon State University, Apr. 2003, 8 pages.
International Search Report and Written Opinion issued by U.S. Patent and Trademark Office as International Searching Authority, in International Application No. PCT/US17/51356, Jan. 18, 2018 (11 pages).
ION, Wikipedia, https://en.wikipedia.org/wiki/Ion, accessed Aug. 30, 2018 (11 pages).
Kirkpatrick, K., "Does saltwater work as mouthwash?", http://health.howstuffworks.com/wellness/oral-care/products/saltwater-as-mouthwash.htm, available online Sep. 18, 2011, accessed Mar. 4, 2019 (6 pages).
Lindeburg, M.R., Chemical Engineering Reference Manual for the PE Exam, Seventh Edition, Professional Publications, Inc., Belmont, California, p. 20-10, 2013 (3 pages).
Marques, M.R.C. et al., "Simulated Biological Fluids with Possible Application in Dissolution Testing", Dissolution Technologies, 18(3):15-28, Aug. 2011 (14 pages).
Metikoš-Huković, M. et al., "Copper Corrosion at Various pH Values with and without the Inhibitor", Journal of Applied Electrochemistry, 30:617-624, 2000 (8 pages).
Michels, H.T. et al., "Copper Alloys for Human Infectious Disease Control", presented at Materials Science and Technology Conference, Pittsburgh, PA, Copper for the 21st Century Symposium, Sep. 25-28, 2005, 11 pages.
Nkonzo, N., "Antimicrobial Copper", International Copper Association, Copper Development Association, May 5, 2010, 6 pages.
Owen, D.H. et al., "A Vaginal Fluid Simulant", Contraception, 59(2):91-95, Feb. 1999 (5 pages).
Perrie, Y. et al., "Chapter 1: Controlling Drug Delivery", *FASTtrack: Pharmaceutics—Drug Delivery and Targeting*, Second Edition, Sample Chapter, 14, Jun. 2012 (26 pages).
Ramachandran, S. et al., "Gluconic Acid: Properties, Applications and Microbial Production", Food Technol. Biotechnol., 44(2):185-195, 2006 (11 pages).

(56) References Cited

OTHER PUBLICATIONS

Roldan, S, et al., "Biofilms and the tongue: therapeutical approaches for the control of halitosis", Clin. Oral Invest., 7:189-197, 2003 (9 pages).

Rosenhein, L.D., "The Household Chemistry of Cleaning Pennies", Applications and Analogies, Journal of Chemical Education, 78(4):513-515, Apr. 2001 (3 pages).

Sawyer, D.T., "Metal-Gluconate Complexes", Chem. Rev., 64(6):633-643, 1964 (11 pages).

Solioz, "Dry Copper Kills Bacteria on Contact", Science Daily, Feb. 22, 2011, 4 pages.

Stein, R., "Gonorrhea Evades Antibiotics, Leaving Only One Drug to Treat Disease", www.npr.org/blogs/health, Aug. 10, 2012, 5 pages.

Wang, et al., "Family Planning Technology", Shanghai Science and Technology Press, p. 334, Dec. 31, 1997 (2 pages)—English Excerpt.

Wikipedia, "Buffer Solution", Wikipedia, the Free Encyclopedia, https://en.wikipedia.org/wiki/Buffer_Solution, accessed Apr. 7, 2017 (8 pages).

Zatcoff, R.C. et al., "Treatment of tinea pedis with socks containing copper-oxide impregnated fibers", The Foot, 18:136-141 (2008) (6 pages).

Dragani, R. "Does Salt Change the pH of Water?", https://sciencing.com/does-salt-change-ph-water-4577912.html., downloaded Dec. 31, 2019, Apr. 19, 2018 (3 pages).

Malik, R. "Warm Saline Rinses", http://www.nature.com/articles/sj.bdj.2009.1093.pdf, accessed Dec. 31, 2019, Br. Dental J., 207(11):520, 2009 (2 page).

VersaBase Cream, Product Information Document, from PCCA, https://pccarx.com/Products/ProductCatalog?pid=30-3641, accessed Dec. 31, 2019 (4 pages).

Wikipedia, "Acetic acid", https://en.wikipedia.org/wiki/Acetic_acid, Oct. 14, 2019 (19 pages).

Wikipedia, "Copper(I) chloride", https://en.wikipedia.org/wiki/Copper(I)_chloride, accessed Oct. 13, 2019 (8 pages).

Wikipedia, "Salt (chemistry)", https://en.wikipedia.org/wiki/Salt_(chemistry), accessed Oct. 14, 2019 (6 pages).

Wikipedia, "Suspension (chemistry)", https://en.wikipedia.org/wiki/Suspension_(chemistry), accessed Oct. 13, 2019 (3 pages).

"Difference Between 304 vs 316 Stainless Steel", Eagle Stainless Tube & Fabrication, Inc., https://eagletube.com/about-us/news/304-vs-316-stainless-steel, Jun. 21, 2018 (2 pages).

Duguid, R., "Copper-inhibition of the growth of oral streptococci and actinomyces", Biomaterials, 4:225-227, Jul. 1983 (3 pages).

European Extended Search Report, issued in European Patent Application No. 17851454.3, dated Jul. 10, 2020 (14 pages).

International Search Report and Written Opinion issued by the U.S. Patent and Trademark Office as International Searching Authority, issued in International Application No. PCT/US2020/17454, dated Jun. 23, 2020 (12 pages).

Maltz, M. et al., "Effect of copper fluoride and copper sulfate on dental plaque, *Streptococcus mutans* and caries in hamsters", Scand. J. Dent. Res., 96:390-392, Oct. 1, 1988 (3 pages).

Moore, R.L. et al., "Evaluating the Anti-Plaque Capabilities of a Copper-Containing Prophylaxis Paste", J. Periodontal., 60(2):78-80, Feb. 1989 (3 pages).

Mulligan, A.M. et al., "The effect of increasing copper content in phosphate-based glasses on biofilms of *Streptococcus sanguis*", Biomaterials, 24:1797-1807, 2003 (11 pages).

European Extended Search Report issued in European Patent Application No. EP20161252.0, dated Jun. 17, 2020 (9 pages).

European Partial Supplementary Search Report issued in EP17851454.3, dated Apr. 6, 2020 (14 pages).

Khaled, K.F., "Studies of the corrosion inhibition of copper in sodium chloride solutions using chemical and electrochemical measurements", Materials Chemistry and Physics, 125:427-433, 2011 (7 pages).

Saxer, U P et al., "New Studies on Estimated and Actual Toothbrushing Times and Dentifrice Use", J. Clin. Dent., 9(2):49-51, 1998 (1 page)—Abstract Only.

Shackel, N.A. et al., "Copper-salicylate gel for pain relief in osteoarthritis: a randomised controlled trial", MJA, 167:134-136, Aug. 4, 1997 (3 pages).

Tamba, B.I. et al., "Common Trace Elements Alleviate Pain in an Experimental Mouse Model", Journal of Neuroscience Research, 91:554-561, 2013 (8 pages).

Yassin, N. et al., "Effect of a topical copper indomethacin gel on inflammatory parameters in a rat model of osteoarthritis", Drug Design, Development and Therapy, 9:1491-1498, 2015 (8 pages).

"10 Homemade Gargles That Heal", Reader's Digest of Canada, www.readersdigest.ca/health/conditions/gaggle-gargles/, Jan. 4, 2008 (3 pages).

"Antimicrobial Copper FAQs", CDA Publication 201, Copper Development Association, Hemel Hempstead, United Kingdom, 2010 (8 pages).

"Buffer Reference Center", https://www.sigmaaldrich.com/life-science/core-bioreagents/biological-buffers/learning-center/buffer-reference-center.html, Oct. 26, 2008 (6 pages).

AZO Materials, "Medical Applications of Stainless Steel 304 (UNS S30400)", azom.com/Articles.aspx?=6641, Aug. 30, 2012 (3 pages).

Blanc, C. et al., "Galvanic coupling between copper and aluminium in a thin-layer cell", Corrosion Science, 52(3):991-995, 2010 (6 Pages).

European Extended Search Report issued in EP20185469.2, dated Oct. 9, 2020 (10 pages).

Fenelon, A.M. et al., "The electrochemical synthesis of polypyrrole at a copper electrode: corrosion protection properties", Electrochimica Acta, 47:4467-4476, 2002 (10 pages).

Google Search "Copper Salt for Sore Throat 'Coronavirus'", dated Aug. 24, 2020 (2 pages).

Gray, L.W. et al., "Urinary Copper Elevation in a Mouse Model of Wilson's Disease Is a Regulated Process to Specifically Decrease the Hepatic Copper Load", PLoS One, 7(6):e38327, Jun. 22, 2012 (11 pages).

Read, A.J., "Dissolution of Copper in Weakly Acidic Solutions", The Journal of Physical Chemistry, 76(24):3656-3663, 1972 (8 pages).

Zwirner, E., "5 Advantages of Vertical Storage Tanks", https://www.zwirnerequipment.com/blog/5-advantages-vertical-storage-tanks/, Oct. 20, 2014 (2 pages).

Beigel, J.H. et al., "Remdesivir for the Treatment of Covid-19—Final Report", The New England Journal of Medicine, 383(19):1813-1826, published online Oct. 9, 2020 (14 pages).

Bianchetti, M. G., et al., "Body fluids and salt metabolism—Part I", Italian Journal of Pediatrics, 35:36, 2009 (6 pages).

CDA Research Group, Inc., "A Double-Blind, Placebo-Controlled, Crossover Study to Evaluate the Efficacy and Tolerability of 3VM1001 Cream for the Treatment of Pain Associated With Post Herpetic Neuralgia: A Proof of Concept Study", Identifier NCT03421613, published on clinicaltrials.gov <URL: https://www.clinicaltrials.gov/ct2/show/NCT03421613>, published Jul. 10, 2018 (8 pages).

CDA Research Group, Inc., "A Double-blind, Placebo-controlled, Randomized Study to Assess the Safety and Efficacy of 3VM1001 Cream for the Treatment of Chronic Pain Caused by Osteoarthritis of the Knee: A Proof of Concept Study", Identifier: NCT02332148, Published on ClinicalTrials.Gov, <URL: https://clinicaltrials.gov/ct2/show/NCT02332148>, Published Aug. 21, 2015 according to ClinicalTrials.Gov (6 pages).

CDA Research Group, Inc., "A Double-Blind, Placebo-Controlled, Randomized Study to Evaluate the Safety and Efficacy of 3VM1001 Cream for the Treatment of Chronic Pain Caused by Osteoarthritis of the Knee: A Dose Ranging Study", Identifier: NCT03142178 published on clinicaltrials.gov <URL: https://www.clinicaltrials.gov/ct2/show/NCT03142178 >, published Jul. 6, 2018 according to ClinicalTrials.Gov (9 pages).

De Rauglaudre, G. et al., "Tolerance of the association sucralfate / Cu-Zn salts in radiation dermatitis", Annales de dermatologie, 1:11-15 (2008)—English Abstract (5 pages).

Robinson, J., "No improvement in mortality rates for COVID-19 patients treated with remdesivir", the Pharmaceutical Journal, DOI:10.1211/PJ.2020.20208045, published online Jun. 8, 2020 (3 pages).

Al-Kharafi, et al., "Selective dissolution of brass in salt water", Journal of Applied Electrochemistry, 34:47-53, 2004 (7 pages).

(56) References Cited

OTHER PUBLICATIONS

Bauer, "Understanding radiation dermatitis", American Nurse Today, 11(1):13-15, Jan. 2016 (3 pages).
Bauer, "Understanding radiation dermatitis", URL<http://old.woundcareadvisor.com/understanding-radiation-dermatitis/>, Wound Care Advisor, vol. 5, No. 3, May/Jun. 2016 (6 pages).
Ben-Hur, et al., "Phosphorus Burns: The Antidote: A New Approach", British Journal of Plastic Surgery, 25:245-249, 1972 (5 pages).
Biocompatible, definition from Cambridge Dictionary, URL <https://dictionary.cambridge.org/us/dictionary/english/biocompatible>, accessed Oct. 26, 2020 (6 pages).
Cancer Facts & Figures 2016, American Cancer Society, URL <https://www.cancer.org/research/cancer-facts-statistics/all-cancer-facts-figures/cancer-facts-figures-2016.html>, 2016 (72 pages).
Cortes, et al., "The use of copper to help prevent transmission of SARS-coronavirus and influenza viruses. A general review", Diagnostic Microbiology and Infectious Disease, 98:115176, available online Aug. 15, 2020 (5 pages).
Google Search, "copper in sea salt", URL <https://www.google.com/search?q=copper+in+sea+salt&ei=TRrWYJyaCemr5NoPvImPiA . . . >, accessed Jun. 25, 2021 (2 pages).
Google Search, "Copper phosphate buffered saline", URL: <https://scholar.google.com/scholar?hl=en&as_sdt=0%2C47&q=copper=+phosphate+buffered . . . >, accessed Aug. 5, 2021 (2 pages).
Google Search, "dead sea salt and acetate buffer mouthwash", URL <https://www.google.com/search?q=dead+sea+salt+and+acetate+buffer+mouthwash&ei=d . . . >, accessed Jun. 25, 2021 (2 pages).
Google Search, "mouthwash dead sea salt and acetate buffer", URL <https://google.com/search?q=mouthwash+dead+sea+salt+and+acetate+buffer&tbm =. . . >, accessed Jun. 25, 2021 (2 pages).
International Search Report and Written Opinion issued by the U.S. Patent and Trademark Office as International Searching Authority, in International Application No. PCT/US21/24555, dated Jul. 8, 2021 (9 pages).
Iqbal, K. et al., "Role of Different Ingredients of Tooth Pastes and Mouthwashes in Oral Health", Journal of the Pakistan Dental Association, 20(03):163-170, Jul.-Sep. 2011 (8 pages).
Pramanik, et al., "A novel study of antibacterial activity of copper iodide nanoparticle mediated by DNA and membrane damage", Colloids and Surfaces B: Biointerfaces, 96:50-55, published online Apr. 5, 2012 (6 pages).
Wikipedia, "Saline (Medicine)", URL <https://en.wikipedia.org/wiki/Saline_(medicine)>, accessed Jul. 21, 2021 (9 pages).
Wong, R. K. S. et al., "Clinical practice guidelines for the prevention and treatment of acute and late radiation reactions from the MASCC Skin Toxicity Study Group", Support Care Cancer, DOI 10.1007/s00520-013-1896-2, published online Aug. 14, 2013 (16 pages).
Physiological Saline, definition from APA Dictionary of Psychology, <URL: https://dictionary.apa.org/physiological-saline[Oct. 5, 2021 11:47:23 AM], 1 page.
Kole, A., et al., "Acute radiation dermatitis in breast cancer patients: challenges and solutions", Breast Cancer —Targets and Therapy, 9:313-323, May 5, 2017 (11 pages).
Leventhal, J., et al., "Radiation Dermatitis: Recognition, Prevention, and Management", Oncology (Williston Park), 31(12):885-887, 894-899, Dec. 15, 2017 (10 pages).
Ryan, J., "Ionizing Radiation: The Good, the Bad, and the Ugly", Author Manuscript published in final edited form as J Invest Dermatol., 132(3 0 2):985-993, Mar. 2012 (16 pages).
Ryan, J., et al., "Curcumin for Radiation Dermatitis: A Randomized, Double-Blind, Placebo-Controlled Clinical Trial of Thirty Breast Cancer Patients", Author Manuscript published in final edited form as Radiat Res., 180(1):34-43, Jul. 2013 (20 pages).
Sims, "'Breast Cancer Isn't Sexy': Woman Shares Post-Radiation Images to Show Reality of Disease", The Independent, <URL: https://www.independent.co.uk/life-style/health-and-families/health-news/breast-cancer-isn-t-sexy-woman-shares-postradiation-images-to-show-reality-of-disease-a6709516.html>, Oct. 26, 2015 (4 pages).
Williams, M., et al., "Phase III double-blind evaluation of an aloe vera gel as a prophylactic agent for radiation-induced skin toxicity", I. J. Radiation Oncology Biology Physics, 36(2):345-349, Sep. 1, 1996 (5 pages).
"VersaBase Cream, Pcca (RX): Ingredients and Reviews", https://www.skinsafeproducts.com/versabase-cream-rx-pcca, accessed Jun. 3, 2022 (5 pages).
Horie, et al., "Inactivation and morphological changes of avian influenza virus by copper ions", Arch Virol, 153:1467-1472, published online Jul. 1, 2008 (6 pages).
Khan, "Taanbey-ka-Kushta", Traditional Knowledge Resource, Traditional Knowledge and Digital Library, Khazaain-al-Advia, vol. II (20th Century Ghani AD), Nadeem Yunus Printer, Sheikh Mohd Basheer & Sons, Lahore, pp. 155-156, 1911 (4 pages).
Madanapala, "Tamra Guna", Traditional Knowledge Resource, Traditional Knowledge and Digital Library, Translated by Rama Prasad, Khemaraj Shri Krishnadas, Prakashan, Bombay, India, p. 98, 1998 (4 pages).
Prausnitz, et al., "Transdermal drug delivery", Author Manuscript published in final edited form as Nat. Biotechnol., 26(11):1261-1268, Nov. 2008 (18 pages).
Shaligram, et al., "Toxicity of copper salts is dependent on solubility profile and cell type tested", Toxicology in Vitro, 27(2):844-851, Mar. 2013, available online Dec. 31, 2012 (9 pages).
Szunerits, et al., "Heat: A Highly Efficient Skin Enhancer for Transdermal Drug Delivery", Frontiers in Bioengineering and Biotechnology, vol. 6, Article 15, Feb. 15, 2018 (13 pages).
Tuck, et al., "3.07—Corrosion of Copper and its Alloys", Shreir's Corrosion, vol. 3, pp. 1937-1973, 2010 (38 pages).
Wright, Un-Spiked Results, Test ID: 05992-001-001, Version Type: Version, Sep. 12, 2017 (1 page).
Aaseth, J. et al., "Chapter 10: Copper (excerpt)", from Handbook on the Toxicology of Metals, Second Edition, vol. II: Specific Metals, Friberg, et al., Eds., Elsevier Science Publishers B.V, Amsterdam, pp. 240-254,1986 (19 pages).
Stokinger, H.E. et al., "Chapter 11: Copper", in Patty's Industrial Hygiene and Toxicology: vol. 2A—Toxicology, Clayton et al., Eds., John Wiley Sons, New York, pp. 1620-1630, 1981 (16 pages).
EPA, "Drinking Water Criteria Document for Copper (Final Draft)", United States Environmental Protection Agency, EPA-600/X-84-190-1, pp. V-1-V-28, Mar. 1985 (38 pages).
"Copper(II) Sulfate, Pentahydrate", ICSC 1416, CAS#: 7758-99-8, EC No. 231-847-6, International Labour Organization, World Health Organization, www.ilo.org/dyn/icsc/showcard.display?p_lang=en&p_card_id=1416&p_version=2, Oct. 2001 (2 pages).
European Extended Search Report issued in European Application No. 20760320.0, dated Oct. 25, 2022 (17 pages).
"About the Study: Elvis Covid-19 Study Full Information", The University of Edinburgh, URL <https://www.ed.ac.uk/usher/elvis-covid-19/about-the-study>, published Jun. 24, 2020 (4 pages).
"CopperFixx Pain Relief Cream—Products", URL:https://web.archive.org/web/20160905175719/http://copperfixx.com/index/php/copperfixx/products/copperfixx-pain-relief-cream.html, Sep. 5, 2016, accessed May 2, 2023 (2 pages).
"Coronavirus: Researchers to trial salt water as Covid-19 treatment", URL <https://www.bbc.com/news/uk-scotland-edinburgh-east-fife-53170734>, Jun. 25, 2020 (2 pages).
Bhunya, et al., "Genotoxicity of an Inorganic Pesticide, Copper Sulphate in Mouse in vivo Test System", Cytologia, 52:801-808, 1987 (8 pages).
Dutton, "Salt Water Vs. Covid-19: Researchers Launch Study to Lessen Symptoms and Duration of Illness", URL <https://www.biospace.com/article/salt-water-vs-covid-19-scottish-researchers-launch-study-to-lessen-symptoms-and-duration-of-illness/>, BioSpace, Jun. 29, 2020 (6 pages).
Radulesco, et al., "Copper enhanced nasal saline irrigations: a safe potential treatment and protective factor for Covid-19 infection?", Rhinology Online, 3:87-88, 2020 (2 pages).
"Chapter 11.7: Crystalline Solids; Crystal Lattices and Unit Cells", in General Chemistry, Ninth Edition, Eds., Ebbing, et al., Houghton Mifflin Company, Boston, pp. 448-450, 2007 (19 pages).
Glaser, et al., "Pilot Study: Absorption and Efficacy of Multiple Hormones Delivered in a Single Cream Applied to the Mucous

(56) References Cited

OTHER PUBLICATIONS

Membranes of the Labia and Vagina", Gynecologic and Obstetric Investigation, 66:111-118, published online Apr. 29, 2008 (8 pages).

* cited by examiner

TOPICAL COPPER ION TREATMENTS AND METHODS OF TREATMENT USING TOPICAL COPPER ION TREATMENTS IN THE DERMATOLOGICAL AREAS OF THE BODY

This Application is a continuation of U.S. patent application Ser. No. 13/842,387, filed on Mar. 15, 2013, and issued under U.S. Pat. No. 10,398,733 on Sep. 3, 2019, the entire contents of which are incorporated herein by reference in their entirety.

BACKGROUND OF THE INVENTION

Field of the Invention

The invention pertains generally to topical treatments containing copper ions and to methods of treating body conditions using topical treatments containing copper ions in various anatomical areas of the body. More particularly, the invention pertains to treating body conditions affecting the dermatological areas using topical treatments containing copper ions.

Brief Discussion of the Related Art

Many various abnormal body conditions are caused by harmful pathogens or microbes, examples of which include bacteria, fungi and viruses. Abnormal body conditions that arise in or affect the genital area in women typically affect the vagina and are commonly referred to as "vaginitis". The term "vaginitis" encompasses infection and/or inflammation of the vagina caused by bacteria, fungi and/or viruses. Vaginitis may extend to the external female genital area, i.e. the vulva, in which case it is usually referred to as "vulvovaginitis". In addition, bacterial, fungal and viral conditions that affect all or part of the genital area in women, i.e. vagina, vulva and/or surrounding anatomical area, may also affect all or part of the rectal (anal) area, i.e. the rectum (anal canal) and surrounding anatomical area. In men, infection and/or inflammation of bacterial, fungal and/or viral origins may affect all or part of the rectal area and also all or part of the genital area, i.e. the penis, scrotum and surrounding anatomical area.

Vaginitis that is bacterial in origin is commonly called "bacterial vaginosis". Many different bacteria are responsible for bacterial vaginosis and some of these bacteria are the cause of sexually transmitted diseases in women and men. Examples of sexually transmitted bacterial diseases that affect the vagina and surrounding anatomical areas are gonorrhea and chlamydia, which appear in the general population on a widespread basis. It is estimated by the Centers for Disease Control and Prevention (CDC) that more than 700,000 people annually in the U.S. alone acquire new gonorrhea infections, According to the CDC, over 1.3 million chlamydia infections were recorded in the U.S. in 2010 alone. In addition, there are a large number of undiagnosed, untreated or unreported infections of gonorrhea and chlamydia because the diseases may be asymptomatic or present with only very mild symptoms. Oftentimes, gonorrhea and chlamydia occur together. Gonorrhea and chlamydia may also appear in the mouth, throat and rectum (anus) in men and women. If left untreated, gonorrhea and chlamydia can spread to the uterus and/or Fallopian tubes and may cause pelvic inflammatory disease (PID), ectopic pregnancies, chronic pelvic pain and increased risk for infection with the human immunodeficiency virus (HIV).

Untreated gonorrhea may also affect the blood, joints and heart valves. The usual treatments for gonorrhea and chlamydia are appropriate antibiotics, but history has demonstrated that over time many bacterial diseases develop a resistance to antibiotics, indeed, according to the CDC, numerous antibiotics previously used to treat gonorrhea have lost their effectiveness, and there is currently only one remaining drug, i.e. the injectable antibiotic ceftriaxone, proven effective for treating gonorrhea There is great concern in the medical community that it is only a matter of time before gonorrhea becomes resistant to this last remaining drug. Other types of pathogens and microbes, such as the bacteria *streptococcus* and *staphylococcus* and the parasitic protozoan trichomonas, may also affect the vagina and surrounding anatomical areas resulting in abnormal biological conditions. As with gonorrhea, *staphylococcus* infections are especially problematic because certain strains of the bacteria have become antibiotic resistant. Infections in the vagina may spread to the uterus, resulting in PID which is often a very painful and serious condition with potentially harmful and permanent complications.

In addition to being susceptible to abnormal body conditions caused by bacteria, the vagina and surrounding anatomical areas are susceptible to various abnormal body conditions caused by viruses and fungi. Viral diseases that arise in or affect the vagina and surrounding anatomical areas include herpes (Types I and II), human papilloma virus (HPV) and HIV, all of which are sexually transmittable. Herpes, HPV and HIV can also be found in the areas of the mouth, skin and rectum (anus). Fungal diseases that arise in or affect the vagina include yeast infections, particularly Candida, and thrush. Fungi are also responsible for abnormal biological conditions in other areas of the body such as the mouth (thrush), feet, skin and nails. There is no cure for herpes and HIV. Anti-viral drugs are available to alleviate herpes symptoms and suppress the herpes virus so that active infections recur less frequently and are of shorter duration, but these drugs are associated with significant side effects. Infection with HPV is usually treated with topical medications, oral medications and/or surgical removal of warts. Complications of HPV infection include increased risk for cervical, rectal and vulvar cancers. Available treatments for HIV are designed to suppress the virus and boost the immune system in hope of avoiding opportunistic infections and delaying or preventing the onset of full-blown acquired immune deficiency syndrome (AIDS). In recent years, it was hoped that a vaginal microbicide get called PRO 2000 would be effective at reducing HIV infection when used shortly before sexual intercourse, but unfortunately the compound was found to be ineffective in a large scale clinical trial. Topical and oral medications are available to treat yeast and other fungal infections, but are limited in effectiveness such that fungal infections are often not eradicated and thus reoccur. The vast majority of abnormal body conditions caused by bacteria, viruses and fungi that affect the genital and/or rectal areas in women also affect the genital and/or rectal areas in men.

In addition to conditions caused by harmful pathogens or microbes hemorrhoids are another abnormal body condition that affects the rectum (anus) in men and women and may cause rectal pain, swelling, discomfort and/or itching. Conventional treatments for hemorrhoids include topical medications and surgery. In addition to harmful microbes and pathogens, sperm are microbes that appear in the vagina after intercourse. Numerous spermicidal contraceptive compounds are available for introduction in the vagina. Typically, these must be introduced in the vagina very shortly before intercourse and are therefore oftentimes inconvenient. When intercourse takes place without contraception and there is concern for an unwanted pregnancy, drugs known as the "morning after pill" or "emergency contraceptives" are sometimes prescribed to prevent pregnancy, but these drugs are not 100% effective and may have undesirable side effects.

Abnormal body conditions of bacterial, viral and fungal origins commonly arise in dermatological areas of the body, i.e. skin and nails. The skin and soft tissue are common sites for infections caused by various bacteria including *staphylococcus, enterobacter, pseudomonas,* and *streptococcus*. Oftentimes, infections develop on the skin at the site of a cut, scratch, abrasion, burn, splinter, boil, pimple, blister, insect bite or other wound or trauma that damages or breaks the skin or provides a point of entry for bacteria and/or other harmful organisms. Viruses such as herpes, shingles and HPV are also the cause of abnormal body conditions on the skin. In particular, herpes causes cold sores (fever blisters), shingles causes painful eruptions, and HPV causes warts on the skin. Other organisms also cause warts on the skin. The skin is susceptible to various fungal conditions, such as "athlete's foot" which commonly occurs on the feet and rashes such as ringworm, infections of the nails, particularly fungal infections of the toenails, are also a common and tenacious problem. The skin is further susceptible to various body conditions resulting from aging, environmental factors and various external and internal causes, such conditions including sun/wind damage, dry skin, age spots, pigmentation, scarring, blisters, boils, cysts, pimples, cuts, scratches, burns, abrasions, splinters, insect bites and stings, animal bites and scratches, ulcers, loss of elasticity or collagen that manifests as wrinkles and sagging skin, acne, and many types of rashes, such as measles, chicken pox, eczema, psoriasis, impetigo and rosacea, due to various underlying external and internal causes. Various topical and oral prescription and non-prescription medications and products are available to treat the foregoing skin conditions, The skin is also a carrier for bacteria, viruses and fungi, seeing as how the skin regularly comes in contact with a plethora of pathogens and microbes. Consequently, many products such as sanitizing hand and body lotions and wipes are available commercially for the purpose of reducing germs on the skin.

The oral-respiratory-otic areas of the body. i.e. mouth, throat, nose, sinuses and ears are also common sites for abnormal body conditions due to the aforementioned pathogens and microbes. In addition, various allergies cause undesirable body conditions that impact the oral-respiratory-otic areas of the body, particularly the throat, nose and sinuses. Asthma is a chronic inflammatory disease of the airways responsible for undesirable conditions. Bacteria, viruses, fungi, allergies and/or asthma are responsible for many unwanted symptoms that appear in the oral-respiratory-otic areas of the body including sore throat, tonsillitis, colds, bronchitis, sinusitis, rhinosinusitis, wheezing, ear infections, earache, pressure in the ears, cold sores, mouth ulcers, canker sores, cough, hoarseness or laryngitis, congestion, runny nose, sneezing, sore gums, periodontal disease, tooth decay and halitosis (bad breath). A vast array of prescription and non-prescription drugs and products are commercially available to treat oral-respiratory-otic conditions.

The prescription drugs and even many of the non-prescription drugs or products used to treat the numerous body conditions described above have many drawbacks including undesirable or potentially harmful side effects, high risk of harm in the event of overdose or improper use. high cost, limited effectiveness, the need for dose medical monitoring, and inconvenience. Moreover, there is presently no single compound or product to treat a wide range of body conditions affecting the genital-rectal areas that include the vagina, rectum (anus), and surrounding anatomical areas, the oral-respiratory-otic areas that include the mouth, throat, airway, nose, sinuses and ears, and the dermatological areas that include the skin and nails, much less a non-pharmaceutical topical treatment that is safe, cost-effective, easy and convenient to use, and capable of being embodied in different forms depending on the intended anatomical area or areas of use.

It has previously been established that copper possesses properties by which it is capable of killing, neutralizing and preventing the growth of human pathogens. It is known that many bacteria identified as human pathogens cannot survive on surfaces of copper metal. U.S. Pat. No. 8,135,468 82 to Fuller et al discloses a joint prosthesis having an implant body with an external surface containing an antimicrobial metal where the antimicrobial metal may be copper. U.S. Patent Application Publications No. US 2012/0071807 A1 and No. US 2012/0089068 A1 to McClure, Jr. disclose wound dressings containing a metal-based antimicrobial agent where the metal-based antimicrobial agent may be a mixture of silver ions and copper ions. Devices having an external surface of copper metal for insertion in the vagina to treat abnormal biological conditions have been proposed by Applicants in U.S. patent applications Ser. No. 12/157,823 filed Jun. 13, 2008 (abandoned), Ser. No. 13/317,230 filed Oct. 12,2011, and Ser. No. 13/464,005 filed May 4, 2012, the entire disclosures of which are incorporated herein by reference.

Topical substances containing particles of copper or its alloys have been proposed for health support uses. A product called "MesoCopper®" sold by Purist Colloids, Inc. is a colloidal copper solution containing nano particles of copper for use on the skin to minimize the appearance of fine lines and wrinkles. Another version of the product is sold as an ingestible mineral supplement. Copper peptides for use on the skin are also commercially available and these require peptides, i.e. small fragments of protein that have an affinity for copper to which they bind very tightly. U.S. Pat. No. 7776,315 B2 to Morariu discloses a topical composition containing, at a minimum, a lipoic acid, a carnitine and a carnosine, where the carnosine may be chelated to zinc or copper ions. The intended use for the topical composition is to improve the appearance of aged skin. U.S. Patent Application Publication No. US2008/0195033 A1 to Eagleson et at discloses use of a metal substance to treat diseases in the body. The metal substance is primarily a colloidal suspension and delivery of the substance to the body may require the use of electricity. Prior to the present invention, it has not been recognized to provide a simple solution containing copper ions for use as a topical treatment to be applied directly to anatomical tissue to treat body conditions and/or for use in conjunction with various carriers including creams, gels, lotions, foams, pastes, other solutions, suppositories, tampons, body wipes, wound dressings, skin patches and suture material to form topical treatments in which the carriers facilitate delivery of the copper ions to contact anatomical tissue depending on the anatomical area or areas of use on the body.

SUMMARY OF THE INVENTION

An aspect of the invention pertains to copper ion treatments for use on dermatological areas of the body including copper ion solutions, creams, lotions, gels, foams, body wipes, wound dressings, skin patches and suture material, each containing copper ions that bring about therapeutic effects when the copper ion treatments are applied to dermatological tissue. The copper ion solution includes a copper ion-containing solution composed of a biocompatible solution and copper ions contained in the biocompatible solution. The copper ion creams, lotions, gels and foams are composed of a base material and an amount of the copper ion-containing solution in the range of 5 percent to 30 percent of the total weight of the copper ion creams, lotions, gels and foams. The body wipes comprise a sheet or layer of material that carries the copper ion-containing solution. The wound dressings have a protective surface for being positioned in contact with a damaged or injured area of the skin, and the protective surface carries a copper ion treatment, such as the copper ion-containing solution, such that the copper ions are delivered to the damaged or injured area of the skin via contact with the protective surface. The skin patches have a drug delivery surface for being placed in contact with the skin, and the drug delivery surface is supplied with a copper ion treatment such that the copper ions are delivered to the skin. The suture material is supplied with a copper ion treatment, such as by being soaked or immersed in the copper ion-containing solution. Then, when the suture material is used to create sutures in anatomical tissue, the copper ions from the copper ion treatment are delivered to the anatomical tissue.

Another aspect of the invention pertains to treating damaged or injured areas of the skin by applying a copper ion treatment to the damaged or injured area such that the copper ions contact the damaged or injured area and bring about therapeutic effects. Damaged or injured areas of the skin treatable with the copper ion treatments include wounds, blisters, boils, warts, cysts, pimples, cuts, internal or external surgical incisions, scratches, burns, ulcers, particularly leg and foot ulcers, abrasions, splinters, insect bites and stings, animal bites and scratches, sunburn and windburn. A damaged or injured area of the skin may be treated by spraying the damaged or injured area with the copper ion-containing solution, wiping the damaged or injured area with the copper ion-containing solution using the body wipe, manually applying a copper ion cream, lotion, gel or foam to the damaged or injured area, or applying the protective surface of the wound dressing to the damaged or injured area. Where the damaged or injured area is a surgical incision or a wound requiring sutures, the damaged or injured area can be treated by using the copper ion suture material to create the sutures.

It is also an aspect of the invention to treat rashes on the skin by applying a copper ion treatment to the rash on the skin such that copper ions contact the area of the rash on the skin and bring about therapeutic effects. Rashes that may be treated using the copper ion treatments include eczema, psoriasis, rosacea, impetigo, ringworm, acne and heat rash. Rashes on the skin may be treated by spraying the copper ion-containing solution on the rash, wiping the area of the rash with the copper ion-containing solution using the body wipe, or manually applying a copper ion cream, lotion, gel or foam to the area of the rash on the skin.

In accordance with another aspect of the invention, a copper ion treatment is applied directly to a cold sore or fever blister, such as those that commonly occur on the lips. The copper cream, lotions or gels are well-suited for this purpose. When the copper ion treatment is applied directly to a cold sore, the copper ions from the copper ion treatments bring about therapeutic effects directed at the cold sore.

The copper ion treatments are also used to improve the appearance of the skin, and the copper ion creams, lotions and gels are well-suited to this purpose. In order to treat the facial skin for cosmetic purposes according to an additional aspect of the invention, the copper ion treatment is applied to the facial skin using the fingers and the treatment is carried out on a regular basis. The copper ion treatment may also be applied to the skin on the neck. The therapeutic effects provided by the copper ions as a result of the copper ion treatment being applied to the skin on the face and/or neck bring about improvement in the appearance of skin affected by wrinkles, sagging, undesirable pigmentation, age spots, dry skin, loss of collagen, and loss of skin tone.

An additional aspect of the invention involves using the copper ion treatment to sanitize areas of the skin. The copper ion-containing solution and the copper ion lotions, gels, foams and body wipes are advantageous for this purpose. When the copper ion treatment is applied to an area of the skin to be sanitized, the copper ions bring about sanitizing effects on the skin including antiseptic, antibacterial, antiviral, antifungal anti-pathogenic and antimicrobial effects.

According to another aspect of the invention, "athlete's foot" is treated using a copper ion treatment. The copper ion creams and lotions are well-suited for this treatment The treatment involves applying the copper ion treatment to the area of one or both feet that is affected by athlete's foot, such that the copper ions from the copper ion treatment contact the affected area and bring about therapeutic effects directed at the athlete's foot infection.

The copper ion treatments are also used to treat nail fungus in accordance with a further aspect of the invention. The copper ion creams are well-suited for this use. Treatment of nail fungus using a copper ion cream involves applying the copper ion cream to the affected nail and using the fingers to rub the copper ion cream into and around the affected nail. The therapeutic effects resulting from the copper ions in contact with the infected nail, particularly the antifungal effect, are thus directed at the fungal infection affecting the nail.

DETAILED DESCRIPTION OF THE INVENTION

Figure 1:
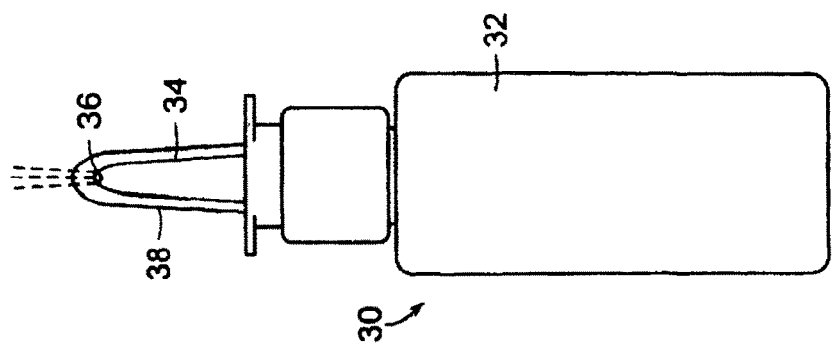
FIG. 1 is a front view of a bottle containing a copper ion treatment and having a spray pump nozzle for dispensing the copper ion treatment.

A solution containing copper ions, i.e. copper ion-containing solution, for use as a topical treatment containing copper ions, i.e. topical copper ion treatment, to treat body conditions is produced according to a process or method by which copper ions from copper metal are leached into an appropriate biocompatible solution. As used herein, "copper metal" means pure copper (99.5% or greater copper after processing) and copper alloys such as brasses, bronzes, copper-nickels and copper-nickel-zincs. Preferably, pure copper is used as the copper metal. Example 1 describes the steps involved in producing an amount of copper ion-containing solution equal or substantially equal to 7.44 ounces.

Example 1

7.44 ounces of biocompatible saline solution buffered with acetic acid and sodium acetate to a pH of 5 (±0.4) is placed in a container or vessel with a tight, removable lid to minimize evaporation. The container is placed in an incubator or oven at a temperature of 37° Celsius (±1° C.). When the saline solution has reached 37° Celsius, 102 grams of pure copper metal in solid form is placed in the heated solution within the container, and the container with the tight lid thereon is placed in the incubator at 37° Celsius for 24 hours. During the 24 hour period, copper ions from the copper metal teach into the solution. At the end of the 24 hour period, the container is removed from the incubator and the copper metal is removed or separated from the solution. The amount of solution remaining after removal or separation of the copper metal therefrom constitutes the copper ion-containing solution and should be essentially 7.44 ounces with minimal evaporation. The copper ion-containing solution produced according to this process contains copper ions in an amount equal or substantially equal to 46 milligrams when analyzed for copper content by inductively coupled plasma/optical emission spectroscopy (ICP/OES). The copper ion-containing solution is stored at room temperature and is ready for use in this form as a topical copper ion treatment to be applied to anatomical tissue to treat body conditions. In addition, the copper ion-containing solution is ready for use in conjunction with various carriers including creams, gels, lotions, foams, pastes, other solutions, suppositories, tampons, body wipes, wound dressings, skin patches and suture material to form topical copper ion treatments in which the carriers facilitate delivery of the copper ion treatments to contact anatomical tissue to treat body conditions.

The solid pure copper metal in Example 1 may be in the form of one or more sheets of pure copper metal, typically in the range of 0.03 to 0.06 inch thick, of appropriate length and width to provide the 102 grams of pure copper metal. In practice, the process described in Example 1 has been carried out using as the copper metal four vaginal therapeutic devices made of pure copper in accordance with Applicants' prior U.S. patent application Ser. No. 13/464,005 previously incorporated herein by reference in its entirety. In this case, each vaginal therapeutic device used was 3.25 inches long by 0.750 inch wide with a wall thickness of 0.031 inch providing 25.5 grams of pure copper. The biocompatible saline solution used in the process described in Example 1 is commercially available from B. Braun Medical. As an alternative to the biocompatible saline, vaginal simulating fluid (VSF) buffered with acetic acid to a pH of 5 (±0.4) can be used as the biocompatible solution, but will produce less leaching of copper ions from copper metal over the 24 hour period. The VSF can be prepared in accordance with published literature, e.g. Owen, D. H., Katz. D. F., "A Vaginal Fluid Simulant", Contraception, pages 91-95 (1999). The process described in Example 1 can be modified to eliminate the step of heating the solution prior to placement of the copper metal therein. In the latter case, the copper metal and unhealed solution are placed In the container, the container with the tight lid thereon is placed in the incubator at 37° Celsius and, once the solution has reached 37° Celsius, the container with the heated solution and copper metal therein is allowed to remain in the oven for 24 hours. The copper metal can be removed or separated from the solution in various ways, such as by lifting the metal out of the solution or pouring the solution alone into another container. Of course, the quantities of biocompatible saline and solid copper mental used in Example 1 can be proportionately increased to produce a greater amount of copper ion-containing solution with each process.

The copper ion-containing solution is believed to have the greatest effectiveness for treating a wide range of body conditions when the solution contains the amount of copper ions leached into the saline from the copper metal over a 24 hour period as described in Example 1. However, it should be appreciated that the process described in Example 1 can be modified to obtain lower copper ion concentrations by adjusting the length of time that the container containing the heated saline and copper metal is allowed to remain in the incubator or oven as explained below in Examples 2, 3 and 4.

Example 2

Follow the steps of Example 1 but allow the container containing the saline and copper metal to remain in the oven at 37° C. for one hour to obtain a copper ion-containing solution that contains an amount of copper ions equal or substantially equal to 8.8 mg.

Example 3

Follow the steps of Example 1 but allow the container containing the saline and copper metal to remain in the even at 37° C. for eight hours to obtain a copper ion-containing solution that contains an amount of copper ions equal or substantially equal to 22 mg.

Example 4

Follow the steps of Example 1 but allow the container containing the saline and copper metal to remain in the oven at 37° C. for 72 hours to obtain a copper ion-containing solution that contains an amount of copper ions equal or substantially equal to 35 mg.

The copper ion-containing solution in its original form, i.e. at the end of the processes of Examples 1-4, can be applied directly to anatomical tissue in various anatomical areas of the body as a copper ion treatment to treat various body conditions. Many types of containers or bottles can be used to hold a quantity of the copper ion-containing solution and to dispense or apply the copper ion-containing solution to anatomical tissue in accordance with the intended anatomical area or areas of use. The copper ion-containing solution may also be used in conjunction with various carriers including creams, lotions, gels, foams, pastes, other solutions, tampons, suppositories, body wipes, wound dressings such as band aids and pads, skin patches, and suture material to form copper ion treatments that facilitate delivery or application of the copper ion-containing solution, and therefore the copper ions, to anatomical tissue. Creams, lotions, gels, foams and pastes may be used when it is advantageous to alter the consistency of the copper ion-containing solution from its original form to obtain a thicker copper ion treatment to facilitate its delivery or application to anatomical tissue. As a result of the copper ions contacting anatomical tissue when the copper ion treatments are applied thereto, local and systemic therapeutic effects are realized including antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. In particular, these effects are realized when the copper ion treatments are used on anatomical tissue in the genital-rectal areas, the oral-respiratory-otic areas and the dermatological areas of the body since the anatomical tissue in these areas is favorable for local and systemic delivery of drugs and medicaments.

In accordance with an aspect of the present invention, the copper ion-containing solution is combined with an appropriate topical cream base to form a copper ion-containing cream, i.e. copper ion cream, in which the amount of copper ion-containing solution is preferably in the range of 5% to 30% by weight of the total weight of the copper ion cream. Examples 5, 6, 7 and 8 pertain to copper ion creams made in accordance with this aspect of the invention using the copper ion-containing solution of Example 1.

Example 5

An appropriate amount of copper ion-containing solution is combined with a biocompatible topical cream base to form a copper ion cream in which the copper ion-containing solution constitutes 5 percent of the total weight of the copper ion cream.

Example 6

An appropriate amount of copper ion-containing solution is combined with a biocompatible topical cream base to form a copper ion cream in which the copper ion-containing solution constitutes 10 percent of the total weight of the copper ion cream, Example 7

An appropriate amount of copper ion-containing solution is combined with a biocompatible topical cream base to form a copper ion cream in which the copper ion-containing solution constitutes 20 percent of the total weight of the copper ion cream.

Example 8

An appropriate amount of copper ion-containing solution is combined with a biocompatible topical cream base to form a copper ion cream in which the copper ion-containing solution constitutes 30 percent of the total weight of the copper ion cream.

Various topical cream bases can be used as the carrier for the copper ion-containing solution in order to form the copper ion creams of Examples 5, 6, 7 and 8, One suitable topical cream base mat can be used is VersaBase® cream made by Professional Compounding Centers of America (PCCA) of Houston, Tex. Another suitable topical cream base that can be used in the copper ion creams is Vanicream® made by Pharmaceutical Specialties, Inc. of Rochester, Minn. The copper ion creams are effective against the body conditions being treated when the only active ingredient in the copper ion creams directed at the underlying condition is the copper ion-containing solution. However, the copper ion creams could contain other ingredients added to the topical cream base that are not active ingredients with respect to the underlying condition being treated such as preservatives, penetrating additives, bioadhesives and stability aids. Preferably, a total weight of at least 70 grams, more preferably 80 grams, of the copper ion creams in the various strengths, i.e. 5 percent, 10 percent, 20 percent and 30 percent of copper ion-containing solution relative to the total weight of the copper ion cream, will be provided for use in containers, bottles, or tubes from which the copper ion creams can be dispensed. It should be appreciated that copper ion creams can be made using the alternative copper ion-containing solutions described above.

According to a further aspect of the present invention, a topical copper ion treatment in the form of a copper ion-containing gel, i.e. copper ion gel, is composed of the copper ion-containing solution and a suitable topical gel base as illustrated below by Examples 9, 10, 11 and 12, which utilize the copper ion-containing solution of Example 1, The amount of the copper ion-containing solution in the copper ion gel is preferably in the range of 5% to 30% by weight of the total weight of the copper ion gel.

Example 9

An appropriate amount of copper ion-containing solution is combined with a biocompatible topical gel base to form a copper ion gel in which the copper ion-containing solution constitutes 5 percent of the total weight of the copper ion gel.

Example 10

An appropriate amount of copper ion-containing solution is combined with a biocompatible topical gel base to form a copper ion gel in which the copper ion-containing solution constitutes 10 percent of the total weight of the copper ion gel.

Example 11

An appropriate amount of copper ion-containing solution is combined with a biocompatible topical gel base to form a copper ion gel in which the copper ion-containing solution constitutes 20 percent of the total weight of the copper ion gel.

Example 12

An appropriate amount of copper ion-containing solution is combined with a biocompatible topical gel base to form a copper ion gel in which the copper ion-containing solution constitutes 30 percent of the total weight of the copper ion gel.

Various topical gel bases can be used as a carrier for the copper ion-containing solution in order to form the copper ion gels. An example of a suitable topical gel base that can be used in Examples 9-12 is VersaBase® gel made by PCCA. As explained above for the copper ion creams, the copper ion gels will be effective when the only active ingredient in the copper ion gels is the copper ion-containing solution, but other ingredients that are inactive with respect to the underlying condition being treated can be added to the topical cream gels. Preferably, a total weight of at least 70 grams, more preferably 80 grams, of the copper ion gels in the various strengths, i.e. 5 percent, 10 percent, 20 percent and 30 percent of copper ion-containing solution relative to the total weight of the copper ion gel, is provided for use in containers, bottles or tubes from which the copper ion gels can be dispensed. Also, copper ion gels can be made using the alternative copper ion-containing solutions. Copper ion gels can be made having a thin, fluidic consistency, and such gels may be used as copper ion serums.

A topical copper ion treatment in the form of a copper ion-containing lotion, i.e. copper ion lotion, according to an additional aspect of the invention is composed of the copper ion-containing solution and a suitable topical lotion base as represented by Examples 13, 14, 15 and 16. Examples 13-16 employ the copper ion-containing solution of Example 1, but copper ion lotions could be made using the alternative copper ion-containing solutions. The amount of the copper ion-containing solution in the copper ion lotion is preferably in the range of 5% to 30% by weight of the total weight of the copper ion lotion. Copper ion gels can be made having a thin, fluidic consistency, and such gels may be used as copper ion serums.

Example 13

An appropriate amount of copper ion-containing solution is combined with a biocompatible topical lotion base to form a copper ion lotion in which the copper ion-containing solution constitutes 5 percent of the total weight of the copper ion lotion.

Example 14

An appropriate amount of copper ion-containing solution is combined with a biocompatible topical lotion base to form a copper ion lotion in which the copper ion-containing solution constitutes 10 percent of the total weight of the copper ion lotion.

Example 15

An appropriate amount of copper ion-containing solution is combined with a biocompatible topical lotion base to form a copper ion lotion in which the copper ion-containing solution constitutes 20 percent of the total weight of the copper ion lotion.

Example 16

An appropriate amount of copper ion-containing solution is combined with a biocompatible topical lotion base to form a copper ion lotion in which the copper ion-containing solution constitutes 30 percent of the total weight of the copper ion lotion, Various topical lotion bases can be used as a carrier for the copper ion-containing solution in the copper ion lotions of Examples 13-16. One suitable topical lotion base that can be used is VersaBase® lotion made by PCCA. As explained above for the copper ion creams and gels, the copper ion lotions will be effective against the body conditions being treated when the only active ingredient in the copper ion lotions is the copper ion-containing solution, but other inactive ingredients could be added to the topical lotion base. Preferably, a total weight of at least 70 grams, more preferably 80 grams, of the copper ion lotions in the various strengths, i.e. 5 percent, 10 percent, 20 percent and 30 percent of copper ion-containing solution relative to the total weight of the copper ion lotion, will be provided for use in containers, bottles or tubes from which the copper ion lotions can be dispensed.

According to another aspect of the present invention, a topical copper ion treatment in the form of a copper ion-containing foam, i.e. copper ion foam, is composed of the copper ion-containing solution and a suitable foam base. Examples 17, 18, 19 and 20 set forth below pertain to copper ion foams or foamable solutions made in accordance with this aspect of the invention using the copper ion-containing solution of Example 1, however copper ion foams or foamable solutions can be made using the alternative copper ion-containing solutions. The amount of the copper ion-containing solution in the copper ion foam or foamable solution is preferably in the range of 5% to 30% by weight of the total weight of the copper ion foam or foamable solution.

Example 17

An appropriate amount of copper ion-containing solution is combined with a biocompatible topical foam base to form a copper ion foam or foamable solution in which the copper ion-containing solution constitutes 5 percent of the total weight of the copper ion foam or foamable solution.

Example 18

An appropriate amount of copper ion-containing solution is combined with a biocompatible topical foam base to form a copper ion foam or foamable solution in which the copper ion-containing solution constitutes 10 percent of the total weight of the copper ion foam or foamable solution.

Example 19

An appropriate amount of copper ion-containing solution is combined with a biocompatible topical foam base to form a copper ion foam or foamable solution in which the copper ion-containing solution constitutes 20 percent of the total weight of the copper ion foam or foamable solution.

Example 20

An appropriate amount of copper ion-containing solution is combined with a biocompatible topical foam base to form a copper ion foam or foamable solution in which the copper ion-containing solution constitutes 30 percent of the total weight of the copper ion foam or foamable solution.

Various topical foam bases can be used as a carrier for the copper ion-containing solution in order to form the copper ion foams or foamable solutions. Depending on the foam base used in Examples 17-20, the combination of foam base and copper ion-containing solution may be in the form of a foam. Alternatively, some foam bases that may be used will result in a foamable solution when combined with the copper ion-containing solution, and the foamable solutions will typically require an appropriate dispenser to create the actual foam. An example of a suitable topical foam base that can be used is VersaBase® foam made by PCCA. When using VersaBase® as the foam base in Examples 17-20, a foamable solution is obtained and requires a foam dispenser to create the foam. As explained above for the copper ion creams, gels and lotions, the copper ion foams will be effective against the body conditions being treated with the only active ingredient therein being the copper ion-containing solution. However, other ingredients that are inactive with respect to the condition being treated can be added to the topical foam base. It is preferred that a total weight of at least 70 grams, more preferably 80 grams, of the copper ion foams or foamable solutions in the various strengths, i.e. 5 percent, 10 percent, 20 percent and 30 percent of copper ion-containing solution relative to the total weight of the copper ion foam or foamable solution, be provided in dispensers from which the copper ion foams can be dispensed.

According to a further aspect of the invention, a topical copper ion treatment in the form of a copper ion-containing paste, i.e. copper ion paste, is composed of the copper ion-containing solution and a suitable paste base. Example 21 set forth below pertains to a copper ion toothpaste made in accordance with this aspect of the invention using the copper ion-containing solution of Example 1, but copper ion pastes can also be made using the alternative copper ion-containing solutions. The amount of the copper ion-containing solution in the copper ion pastes is preferably in the range of 5% to 30% by weight of the total weight of the copper ion paste.

Example 21

An appropriate amount of copper ion-containing solution is combined with a toothpaste base material to form a copper ion toothpaste in which the copper ion-containing solution constitutes in the range of 5 percent to 30 percent of the total weight of the copper ion toothpaste.

The toothpaste base material used in Example 21 can be a commercially available toothpaste including any of the toothpastes marketed and sold under the major brand names. A toothpaste made in accordance with Example 21 is advantageous for treating bad breath, sore gums, gum disease and tooth decay when used on a daily basis in place of a person's regular toothpaste.

According to a further aspect of the invention, the copper ion-containing solution can be combined with various base solutions to form alternative copper ion solutions. Example 22 set forth below pertains to a copper ion mouthwash made in accordance with this aspect of the invention using the copper ion-containing solution of Example 1, but copper ion solutions can also be made using the alternative copper ion-containing solutions of Examples 2-4. The amount of copper ion-containing solution in the alternative copper ion solution is preferably in the range of 5% to 30% by weight of the total weight of the alternative copper ion solution.

Example 22

An appropriate amount of copper ion-containing solution is combined with a mouthwash base solution to form a copper ion mouthwash in which the copper ion-containing solution constitutes in the range of 5 percent to 30 percent of the total weight of the copper ion mouthwash.

The mouthwash base solution used in Example 22 can be a commercially available mouthwash including any of the mouthwashes marketed and sold under the major brand names, A mouthwash made in accordance with Example 22 is advantageous for treating bad breath, sore gums, periodontal disease and tooth decay when used on a daily basis.

The examples described above pertaining to carriers in the nature of lotions, gels, foams and other solutions are particularly well suited for creating copper ion treatments in the nature of copper ion soaps by using as carriers lotion, gel, foam or other solution bases containing a soap component. The copper ion soaps could be designed for use as body soaps or as dish soaps.

FIG. 1 depicts a device 10 useful for dispensing the copper ion treatments, particularly the copper ion-containing solutions in their original form, e.g. the form resulting from Examples 1-4, and the copper ion lotions. The device 10 comprises a container or bottle 12 for holding the copper ion-containing solution and having a spray pump nozzle 14 with an outlet orifice 16. The spray pump nozzle 14 is resiliency biased, typically by a spring, in an upward direction away from the container 12 but is depressible in a downward direction toward the container 12 to effect the spray pump action. Each time the spray pump nozzle is manually depressed the full amount, typically using a finger of the hand holding the container, a predictable amount of copper ion-containing solution is discharged in the form of a spray or stream from the outlet orifice 16. The container 12 may include a removable protective cover 18 for being disposed over the spray pump nozzle 14 between uses. In use, the outlet orifice 16 is placed in line with anatomical tissue to be treated at a close enough distance that the tissue is within the range of the spray or stream dispensed from the outlet orifice. The spray pump nozzle 14 is then depressed the full amount using a finger, causing the predictable amount of copper ion-containing solution to be delivered or sprayed onto the anatomical tissue. The spray pump nozzle 14 can, of course, be depressed multiple times to deliver multiple sprays or streams of the copper ion-containing solution to the tissue. The device 10 is particularly useful for dispensing the copper ion-containing solution in its original form to contact anatomical tissue within the mouth and throat, anatomical tissue of the skin, and anatomical tissue of the external genital and rectal areas. The device 10 could also be adapted to dispense the copper ion lotions, although in such case the copper ion lotions would typically be dispensed in the form of a ribbon, mass or stream of material. In the latter case, the copper ion lotions could be dispensed directly on the tissue to be treated, or on the palm or fingers of a hand which is then used to apply the lotions on the tissue to be treated. The copper ion lotions may be best suited for use on the skin, on the external genital and rectal areas, and in the vagina.

Figure 2:
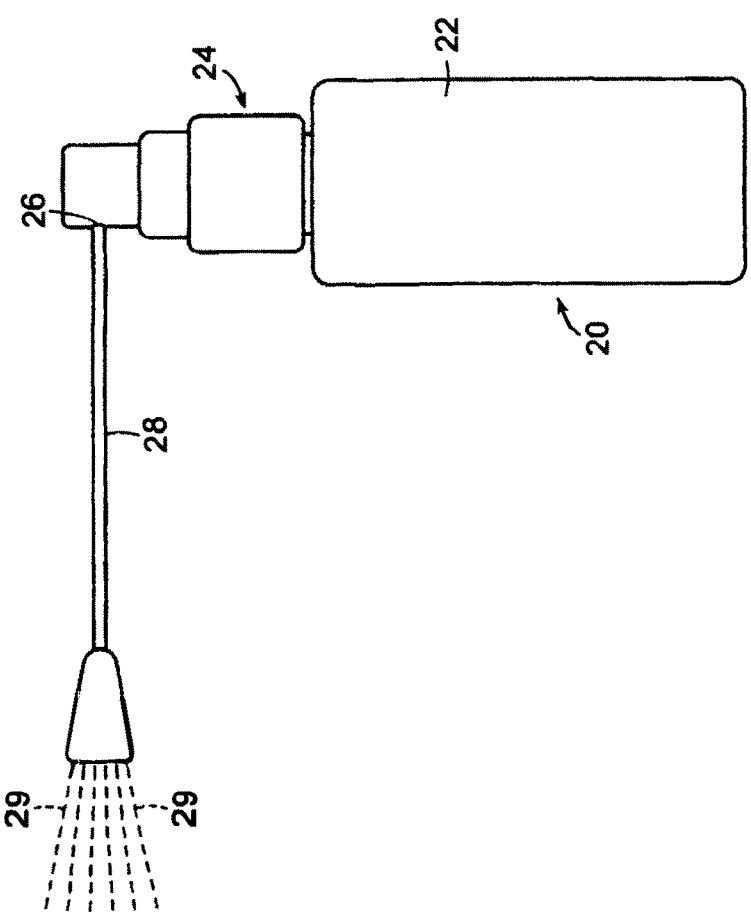
FIG. 2 is a side view of a bottle containing a copper ion treatment and having a spray pump nozzle with an elongate extension for dispensing the copper ion treatment.

Another device 20 useful for dispensing the copper ion treatments, particularly the copper ion-containing solution in its original form, is shown in FIG. 2. The device 20 is similar to the device 10 and comprises a container or bottle 22 having a spray pump nozzle 24 with an outlet orifice 26. The device 20, however, further includes an elongate hollow extension 28 attached to the spray pump nozzle 24. The extension 28 has a first end coupled with the outlet orifice 28 of the spray pump nozzle 24 and has an opposed second end with a wider end surface having a discharge opening 29. Preferably, a plurality of discharge openings 29 are provided along the wider end surface as shown in dotted lines in FIG. 2 to obtain a wider spray pattern as indicated by dotted lines. Each time the spray pump nozzle 24 is manually depressed the full amount, a predictable amount of copper ion treatment is released in spray form from the discharge openings 29 at the end of the extension 28. The wider end surface arid plurality of discharge openings at the second end of the extension provides a wider spray pattern than the device 10. The device 20 could be designed without the spray pump nozzle, with the container 22 being squeezable to force the copper ion treatment to be discharged from the discharge opening(s) 29. The extension 28 may be selectively detachable/attachable to the spray pump nozzle 24 for ease of storage of the device 20. The device 20 may include a removable protective cover (not shown) for being placed over the nozzle 24 between uses. The device 20 is particularly useful as an atomizer for dispensing the copper ion treatments to contact anatomical tissue deeper within the mouth, throat and airway.

Figure 3:
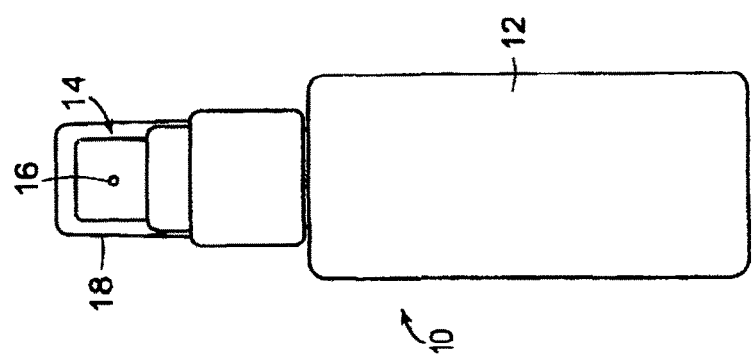
FIG. 3 is a side view of a bottle containing a copper ion treatment wherein the bottle is squeezable to dispense the copper ion treatment from a dropper on the bottle.

The device 30 depicted in FIG. 3 is also useful for dispensing the copper ion treatments, particularly the copper ion-containing solution in its original form. The device 30 comprises a squeezable container or bottle 32 for holding the copper ion treatment and having a tapered dropper or extension 34 with an outlet orifice 36 attached to a cap on the container 32. In use, the container 32 is positioned so that the outlet orifice 36, which is located at the tip of the dropper, faces anatomical tissue to be treated. The container 32 is then squeezed with the fingers and, in response to such finger pressure, individual drops of a predictable amount of copper ion treatment are released from the outlet orifice 36. Alternatively, the extension 34 can be designed to discharge the copper ion treatment in the form of a spray as shown in dotted lines in FIG. 3, which would be particularly useful as a nasal/ear spray. The tapered configuration of the dropper/extension 34 facilitates its placement in the nostril (nasal cavity) and ear (ear canal). The container 32 may include a removable protective cover 38 for being disposed over the dropper 34 between uses. The device 30 is particularly useful for dispensing the copper ion treatments to contact anatomical tissue within the nose (nostrils) and ears (ear canal), and on the skin and nails.

Figure 4:
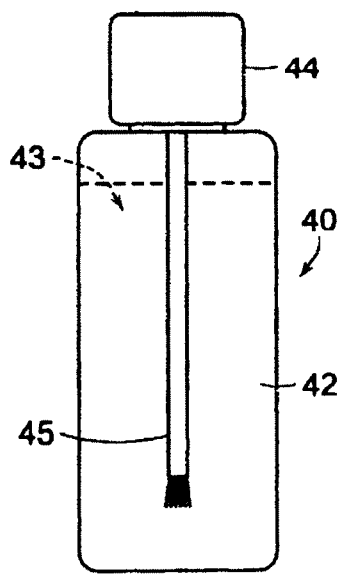
FIG. 4 is a side view of a bottle containing a copper ion treatment and having a brush for applying the copper ion treatment to anatomical tissue.

An additional device 40 for dispensing the copper ion treatments is shown in FIG. 4. The device 40 comprises a container or bottler 42 for holding the copper ion treatment and having a removable cap 44 with a brush 45 attached to an underside of the cap. Typically, the cap 44 will be screwed onto a neck of the container 42. When the cap 44 is disposed on the container 42, the brush 45 extends into the container and is disposed within the copper ion treatment 43. Upon removal of the cap 44 from the container 42, the cap 44 may be manipulated using the fingers and hand to contact anatomical tissue to be treated with the brush 45 in order to deposit the copper ion treatment from the brush 45 onto the anatomical tissue. The device 40 would be particularly useful for applying the copper ion treatments on the skin and nails. The brush 45 could be eliminated from the cap 44, in which case the device 40, if sized appropriately, would be advantageous for holding a copper ion solution such as a copper ion mouthwash.

Figure 5:
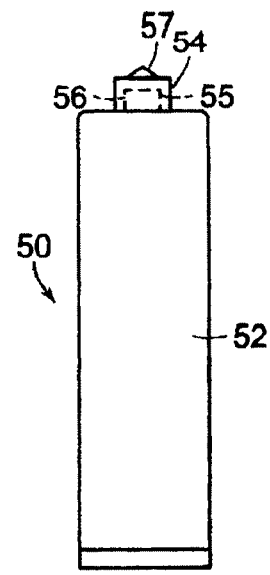
FIG. 5 is a side view of a tube containing a copper ion treatment wherein the tube is squeezable to dispense the copper ion treatment.

The device 50 illustrated in FIG. 5 is particularly useful for dispensing the copper ion treatments formed as creams, lotions, gels and pastes. The device 50 comprises a container 52 in the form of a squeezable tube for holding the copper ion treatment and having a removable cap 54 disposed on an open end or neck 56 of the tube. Typically the cap 54 will be threaded onto an external thread 55 on the neck 56 of the tube. The cap 54 may optionally have a piercing formation 57 that may be used to puncture an optional seal covering the open neck 56 prior to the first use. Upon removal of the cap 54, the piercing formation 57 is placed against the seal, and the cap 54 is pushed in the direction of the tube 52 to puncture the seal Once the seal is penetrated, the tube 52 can be squeezed, preferably from the bottom of the tube working upward, causing the copper ten treatment to be dispensed from the open neck 58 of the tube. The device 50 is particularly well suited for dispensing the copper ion treatments onto the fingers or palm of a hand that is then used to apply the treatments to anatomical tissue, particularly the tissue of the skin and the external genital and rectal areas. However, the copper ion treatments could be squeezed directly on the anatomical tissue to be treated. In addition, when the copper ion treatment is in a paste or other suitable form for use as a toothpaste, the device 50 is particularly well suited for dispensing the copper ion treatment onto a tooth brush in a conventional manner. As explained further below, the device 50 is particularly well suited for use with a vaginal applicator.

Figure 6:
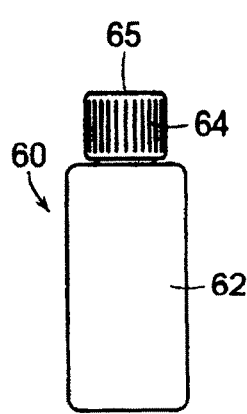
FIG. 6 is a side view of an alternative bottle that is squeezable to dispense a copper ion treatment and showing the bottle in a closed condition.
Figure 7:
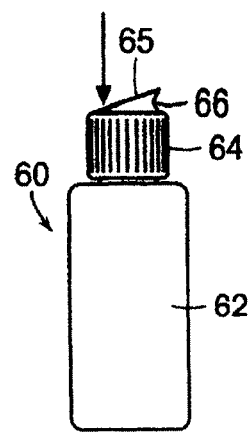
FIG. 7 is a side view of the bottle of FIG. 6 showing the bottle in an open condition.

FIGS. 6 and 7 depict an additional device 60 useful for dispensing the copper ion treatments. The device 60 is particularly advantageous for dispensing copper ion lotions. The device 80 comprises a container or bottle 82 for holding the copper ion treatment and having a cap 64 disposed on an open end or neck of the bottle. The cap 64 could be removable or non-removable. The top surface of the cap 64 is formed by a pivotable member or disc 65 having an outlet orifice 66 along a side edge thereof. FIG. 6 depicts the cap 64 in its closed condition wherein the pivotable member 65 is in a horizontal position relative to the cap 64 and the outlet orifice 66 is disposed within the cap 64 and is not exposed. When the pivotable member 66 is depressed downwardly toward the container 62 at a location opposite the outlet orifice 66 as shown by the arrow in FIG. 7, the cap 64 will assume the open condition shown in FIG. 7 wherein the pivotable member 65 is disposed at an angle relative to the cap 64 and the outlet orifice 66 is in an exposed position located slightly above the cap 64. In use, the pivotable member 85 would be depressed using pressure applied with one or more fingers of the hand. With the cap 64 in the open condition as shown in FIG. 7, the container 82 can be squeezed manually to dispense the copper ion treatment therein from the outlet orifice 86. The cap 64 is returned to the closed position by pressing downwardly on the pivotable member 85 at a location adjacent the outlet orifice. The device 80 is advantageous for dispensing the copper ion treatments onto the palm of the hand or fingers used to apply the treatment to anatomical tissue to be treated, but the device 80 could be used to dispense the copper ion treatments directly on the anatomical tissue to be treated.

Figure 8:
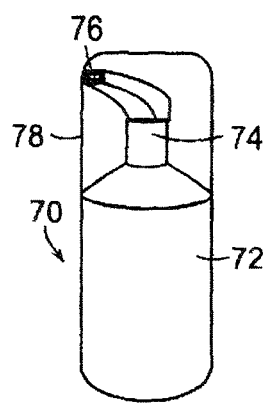
FIG. 8 is a side view of a bottle containing a copper ion treatment and having a pump nozzle for dispensing the copper ion treatment in the form of foam.
Figure 9:
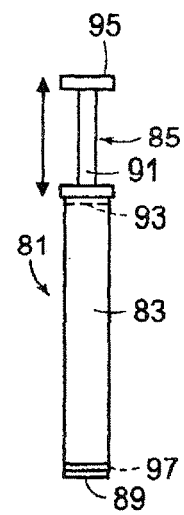
FIG. 9 is a side view of an applicator for delivering a copper ion treatment to the vagina.
Figure 10:
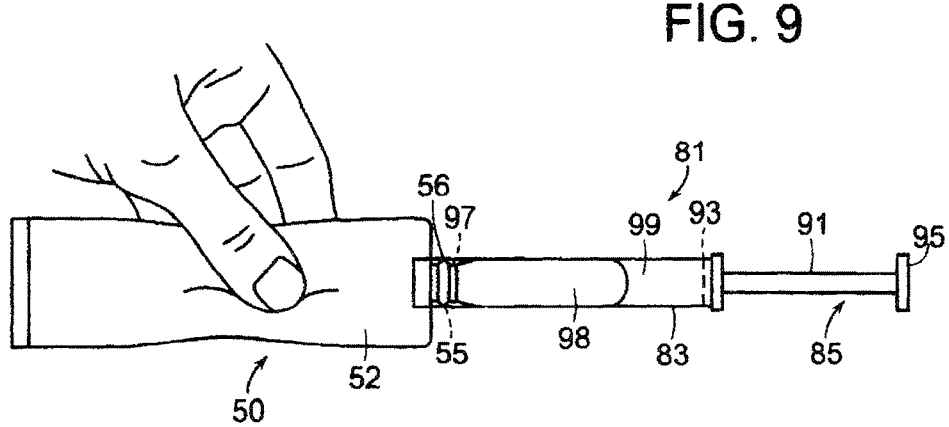
FIG. 10 is a side view of the applicator of FIG. 9 showing use of the applicator in conjunction with the tube of FIG. 5.

The device 70 shown in FIG. 8 is an example of a device that can be used to dispense the copper ion treatment in the form of a copper ion foam. The device 70 comprises a container 72 for holding the copper ion foam or foamable solution and having a resiliently biased foam pump dispenser 74 with an outlet orifice 76. When the foam pump dispenser 74 is depressed the full amount in a manner similar to the device 10, a predictable amount of the copper ion foam is discharged through the outlet orifice 76. If necessary, the device 70 may include a mechanism for creating foam as the copper ion treatment is discharged therefrom. The device 70 may have a removable protective cover 78 for being disposed over the foam pump dispenser 74 between uses. The device 70 could also be adapted to dispense copper ion lotions and gels, FIG. 9 depicts a vaginal applicator 81 useful for delivering the copper ion treatments to the vagina. The vaginal applicator 81 is particularly useful in conjunction with the device 50 as depicted in FIG. 10. Also, the vaginal applicator 81 is particularly well suited for use when the copper ion treatments are in the form of either lotion, cream or gel. The vaginal applicator 81 comprises a hollow barrel 83 and a plunger 85 slidably mounted in the hollow barrel 83. The barrel 83 has an open forward end defining a discharge opening 89 and has a rearward end wall through which a stem 91 of the plunger passes. The stem 91 is attached at one end thereof to an internal flange 93 disposed within the barrel in close, sealing relation therewith. The plunger has a finger flange 95 attached to an opposite end of the stem 91 that is disposed external of the barrel 83, the flange 95 being engageable with a finger or fingers of a hand in order to selectively depress and withdraw the plunger 85 relative to the barrel 83. For use with the device 50, the forward end of the barrel 83 is provided with an internal thread 97 to threadedly engage with the external thread 55 on the neck 58 of the tube 52.

FIG. 10 illustrates the vaginal applicator 81 being filled with the copper ion treatment from the tube 52 of the device 50, As seen in FIG. 10, the cap 54 is removed from the neck 56 of the tube 52, and the forward end of the barrel 83 is threaded onto the neck 56 via threaded engagement of the threads 55 and 97. At this stage, the plunger 85 is fully withdrawn relative to the barrel 83 such that the internal flange 93 is in abutment with the rearward end wall of the barrel 83. The tube 52 is then squeezed using pressure from the fingers in order to dispense the copper ion treatment, represented at 98, into the barrel 83 from the open neck 56 of the tube 52. When the barrel 83 is sized for a particular dosage of copper ion treatment, a sufficient amount of copper ion treatment can be dispensed from the tube 52 to entirely fill the space within the barrel 83 from the neck of the tube 58 to the internal flange 93 which is in abutment with the rearward end wall of the barrel. Alternatively, an indicia or other marking 99 can be provided on the barrel 83 to indicate the point to which the barrel 83 should be filled with copper ion treatment 98 from the tube 52. It is preferred that filling the space within the barrel from the neck of the tube to the internal flange corresponds to a dose of 5 grams of the copper ion treatment. Once the barrel 83 has been filled with the appropriate amount of copper ion treatment 98, the barrel 83 is disengaged from the neck 58 of the tube 52 by disengaging the thread 97 from the thread 55. In order to dispense the copper ion treatment 98 from the applicator 81, the finger flange 95 of the plunger 85 is depressed toward the barrel 83 using a finger, thereby causing the internal flange 93 to push the copper ion treatment 98 through the discharge opening 89 as the plunger 85 is depressed relative to the barrel 83. When the finger flange 95 meets the rearward end wall of the barrel 83, the copper ion treatment 98 will be fully discharged from the applicator. It should be appreciated that the applicator 81 could be used in conjunction with other devices for supplying the copper ion treatments to the barrel 85. It should also be appreciated that the applicator 81 can be supplied for use pre-filled with copper ion treatment 98, in which case the forward end of the barrel would be provided with a removable cap or seal. The applicator 81 is particularly advantageous for supplying the copper ion treatments to the vagina. Accordingly, prior to depressing the plunger 85 to discharge the copper ion treatment 98 from the barrel 83, the forward end of the barrel 83 would be introduced into the vagina until the rearward end of the barrel was located near the entrance to the vagina. Then, upon depressing the plunger 85, the copper ion treatment 98 is discharged from the discharge opening 89 into the vagina.

Figure 11:
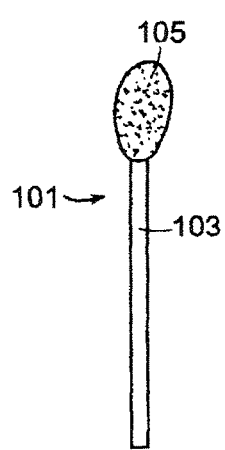
FIG. 11 is a side view of an alternative applicator for applying a copper ion treatment onto anatomical tissue.

Another type of applicator useful in applying the copper ion treatments to anatomical tissue is shown at 101 in FIG. 11. The applicator 101 is in the nature of a swab comprising a handle 103 and a body of absorbent material 105 at an end of the handle 103. The applicator 101 can be used in conjunction with a container or bottle containing a copper ion treatment, such as the device 40 of FIG. 4. Upon removal of the cap 44 from the bottle 42 of the device 40, the handle 103 of the applicator 101 can be grasped with a hand used to manipulate the applicator 101 in order to dip the body of absorbent material 105 into the copper ion treatment within the bottle 42. The body of absorbent material 105 can then be gently contacted with anatomical tissue to be treated thereby causing the copper ion treatment carried by the absorbent body 105 to be deposited on the anatomical tissue to be treated. The applicator 101 is best suited for applying copper ion treatments to localized areas of the skin, nails, ear canal, nostrils, mouth and throat Of course, it should be appreciated that swab applicators 101 can be provided in sealed packages with the bodies of absorbent material 105 pre-supplied with copper ion treatment.

Another type of carrier that can be used to deliver copper ion treatments to the vagina is a tampon. The tampon used can be a commercially available tampon or one similar thereto. The tampon can be one having an applicator including a barrel containing the absorbent tampon body and a plunger slidable within the barrel to dispose or eject the absorbent tampon body from an open forward end of the barrel once the forward end has been introduced in the vagina an appropriate distance in a commonly known manner of tampon use. In this case, an appropriate amount of copper ion treatment can be supplied to the absorbent tampon body via the open forward end of the barrel prior to introduction of the applicator in the vagina and ejection of the absorbent tampon body from the applicator into the vagina. Another suitable tampon can be one without an applicator, i.e. a digital tampon, where the absorbent tampon body is inserted in the vagina by pushing it with the fingers. In this case, the appropriate amount of copper ion treatment is simply deposited on the absorbent tampon body prior to its insertion in the vagina. In both cases, unless the tampon is going to be inserted in the vagina immediately or soon after the absorbent tampon body has been provided with the appropriate amount of copper ion treatment, the tampon should be stored in a sealed container or package until the time of its use in order to avoid evaporation of the copper ion treatment, it should be appreciated that tampon bodies to which the copper ion treatment has been supplied can be provided in sealed containers or packages, with or without an applicator, as a ready-to-use commercial product. Alternatively, the appropriate amount of copper ion treatment may be deposited by the user on the absorbent tampon bodies of tampons sold separately or in conjunction with the copper ion treatment. Preferably, the tampon bodies are supplied with an amount of copper ion-containing solution in the range of 5 to 10 milliliters.

Figure 12:
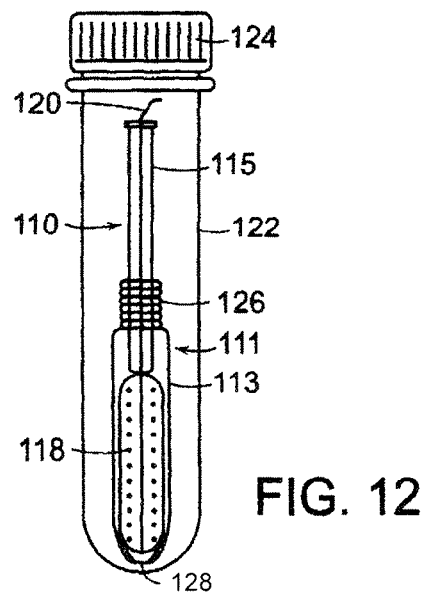
FIG. 12 is a side view of a tampon having a tampon body used as a carrier to deliver a copper ion treatment to the vagina.

FIG. 12 illustrates a tampon 110 according to an aspect of the present invention including an applicator 111 having a hollow barrel 113 and a hollow plunger 115, and an absorbent tampon body 118, to which the appropriate amount of copper ion treatment has been supplied, disposed in the barrel 113 with the string 120 of the tampon body extending from a rear end of the plunger 115. The plunger 115 is slidable within and toward the barrel 113 to push the tampon body 118 and eject it from an open forward end 128 of the barrel. The forward end 128 of the barrel 113 can be tapered to facilitate introduction and advancement in the vagina and can be provided with slits that expand as the tampon body 118 passes therethrough. The tampon 110 is provided in an air-tight container or bottle 122 having a removable cap or lid 124. In order to use the tampon 110, the lid 124 is removed from the bottle 122 and the tampon 110 is removed from the bottle. The tampon 110 is inserted in the vagina in a conventional manner of using tampons. More specifically, the applicator 111 is held by grasping a finger grip 126 on the barrel 113, and the forward end 128 of the barrel is inserted in the vagina. The applicator 111 is advanced into the vagina until the fingers grasping the finger grip 126 touch the entrance to the vagina. The plunger 115 is then pushed into the barrel 113, thus causing the tampon body 118 to be ejected from the forward end 128 of the barrel into the vagina. The applicator 111 is then withdrawn from the vagina and discarded, leaving the tampon body 118 in place in the vagina. Once the tampon body 118 is in place in the vagina, the copper ion treatment carried by the tampon body contacts the anatomical tissue of the vagina and leaks into the vaginal fluid normally present in the vagina. The tampon body 118 is removed from the vagina at the appropriate time by grasping and pulling on the string 120. Examples of tampons according to an aspect of the invention are described below in Examples 23 and 24.

Example 23

A tampon for delivering a copper ion treatment to the vagina is prepared by supplying 5 milliliters of a copper ion-containing solution to an absorbent tampon body intended to be introduced into the vagina.

Example 24

A tampon for delivering a copper ion treatment to the vagina is prepared by supplying 10 milliliters of a copper ion-containing solution to an absorbent tampon body intended to be introduced into the vagina.

The copper ion-containing solution used in Examples 23 and 24 is the copper ion-containing solution in its original form as obtained in accordance with the method set forth in Example 1. However, it should be appreciated that tampons can be provided in which the tampon bodies are supplied with the alternative copper ion-containing solutions or other forms of the copper ion treatments.

Another type of carrier useful to deliver the copper ion treatments to the vagina and rectum is a suppository. Suppositories are commonly used in the vagina and rectum (anus) as a means for dispensing various active ingredients or medicaments. Suppositories are made in various shapes including oviform, globular, conical and bullet shapes, and in various sizes. Suppositories typically weigh in the range of 1 to 5 grams. Suppositories can be solid bodies composed of a mixture of a suitable suppository base material and the active ingredients or medicaments. Alternatively, suppositories can be made with a solid outer wall of suppository base material enclosing non-solid active ingredients or medicaments. The suppository base materials used in suppositories allow them to dissolve or melt when exposed to the moisture (body fluid) or heat (body temperature) found in the vagina or rectum (rectal or anal canal), thereby releasing the active ingredients or medicaments into the vagina or rectum. Suitable suppository base materials include oleaginous (fatty) base materials, including cocoa butter, theobroma oil and synthetic triglycerides, or water soluble or miscible base materials, including glycerinated gelatin and polyethylene glycol (PEG) polymers. It is preferred that the base materials be non-toxic, non-irritating, inert, and biocompatible. Suppositories suitable for use in an aspect of the present invention can be prepared in various ways according to conventional methods for preparing suppositories including compression molding and fusion molding. Suppositories for use as vaginal and rectal suppositories according to an aspect of the present invention are preferably made in two different sizes, i.e. a suppository weighing 3 grams and a suppository weighing 5 grams, to accommodate different sizes of vaginal and rectal anatomy. Each size suppository can be made in different strengths based on the percentage by weight of the active ingredient, i.e. the copper ion treatment, relative to the total weight of the suppository. Preferably, the amount of copper ion-containing solution in the suppository is in the range of 5% to 30% of the total weight of the suppository. The suppositories are preferably formed in plastic molds and can be stored at room temperature. The suppositories will be effective against the body condition being treated when the only active ingredient contained in the vaginal and rectal suppositories is the copper ion treatment. However, the vaginal and rectal suppositories could contain additional ingredients that are inactive with respect to the underlying condition or conditions being treated, such as preservatives, penetrating additives, bioadhesives and stability aids. The suppositories may be inserted in the vagina and rectum using the fingers, or the suppositories may be provided with applicators to facilitate insertion thereof in the vagina and rectum. Examples of vaginal and rectal suppositories according to an aspect of the invention are set forth in Examples 25-32, which utilize the copper ion-containing solution of Example 1. However, the alternative copper ion-containing solutions could be used in Examples 25-32.

Example 25

A suppository base material is combined with an appropriate amount of copper ion-containing solution and is molded into a suppository for vaginal or rectal use having a total weight of 3 grams, wherein the copper ion-containing solution constitutes 5 percent of the total weight of the suppository.

Example 26

A suppository base material is combined with an appropriate amount of copper ion-containing solution and is molded into a suppository for vaginal or rectal use having a total weight of 3 grams, wherein the copper ion-containing solution constitutes 10 percent of the total weight of the suppository.

Example 27

A suppository base material is combined with an appropriate amount of copper ion-containing solution and is molded into a suppository for vaginal or rectal use having a total weight of 3 grams, wherein the copper ion-containing solution constitutes 20 percent of the total weight of the suppository.

Example 28

A suppository base material is combined with an appropriate amount of copper ion-containing solution and is molded into a suppository for vaginal or rectal use having a total weight of 3 grams, wherein the copper ion-containing solution constitutes 30 percent of the total weight of the suppository.

Example 29

A suppository base material is combined with an appropriate amount of copper ion-containing solution and is molded into a suppository for vaginal or rectal use having a total weight of 5 grams, wherein the copper ion-containing solution constitutes 5 percent of the total weight of the suppository.

Example 30

A suppository base material is combined with an appropriate amount of copper ion-containing solution and is molded into a suppository for vaginal or rectal use having a total weight of 5 grams, wherein the copper ion-containing solution constitutes 10 percent of the total weight of the suppository.

Example 31

A suppository base material is combined with an appropriate amount of copper ion-containing solution and is molded into a suppository for vaginal or rectal use having a total weight of 5 grams, wherein the copper ion-containing solution constitutes 20 percent of the total weight of the suppository.

Example 32

A suppository base material is combined with an appropriate amount of copper ion-containing solution and is molded into a suppository for vaginal or rectal use having a total weight of 5 grams, wherein the copper ion-containing solution constitutes 30 percent of the total weight of the suppository.

Figure 14:
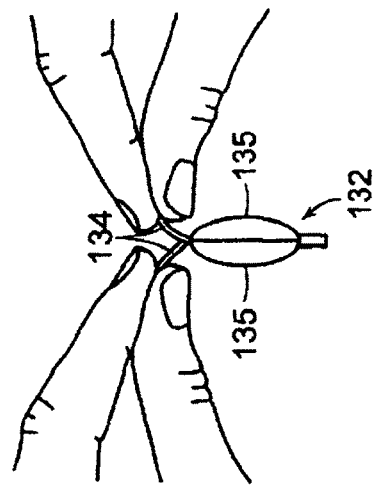
FIG. 14 is a side view showing a suppository of FIG. 13 being removed from its package.
Figure 13:
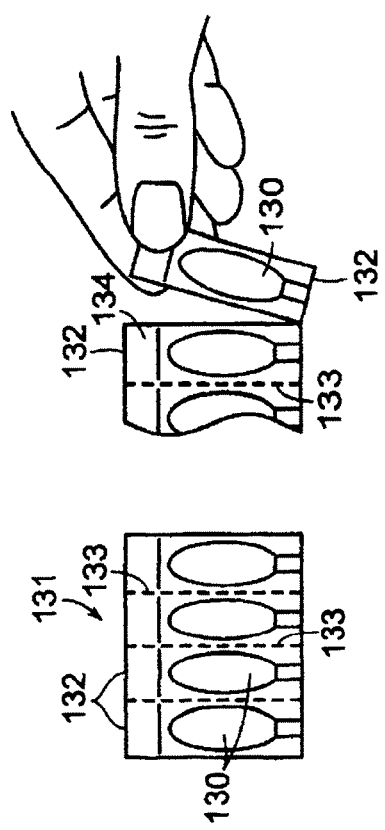
FIG. 13 is a broken front view of a plurality of suppositories containing a copper ion treatment the suppositories being insertable in the vagina or rectum to deliver the copper ion treatment to the vagina or rectum.

FIG. 13 illustrates a strip 131 of interconnected packages or pods 132, each enclosing a vaginal or rectal suppository 130 containing a copper ion treatment. The pods 132 are separated from each other by a perforation fine 133 allowing the pods 132 to be detached from each other by tearing along the perforation fines 133 as depicted in FIG. 13. Each pod 132 has front and rear walls 135 between which a suppository 130 is retained. The front and rear waifs 135 are sealed to one another along their peripheral edges. As shown in FIG. 14, each pod 132 is provided with a pair of finger tabs 134 respectively attached to the front and rear walls 135, the finger tabs 134 being capable of being pulled in opposite directions using the fingers to separate the opposed waits 135 and thereby release the suppository 130 contained therein.

Figure 15:
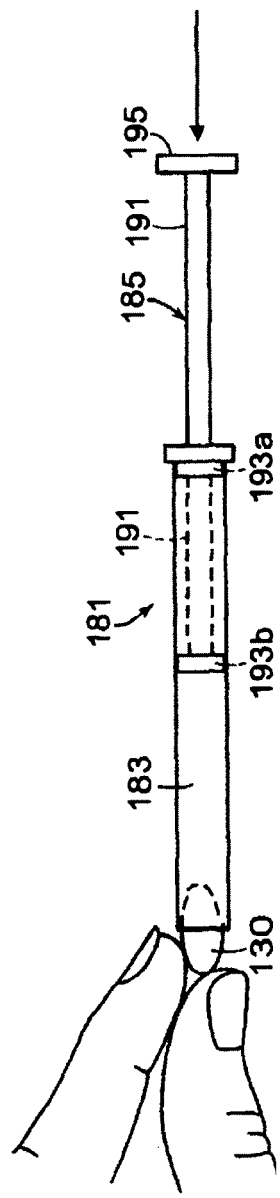
FIG. 15 is a side view of an applicator for delivering the suppositories of FIG. 13 to the vagina or rectum.
Figure 16:
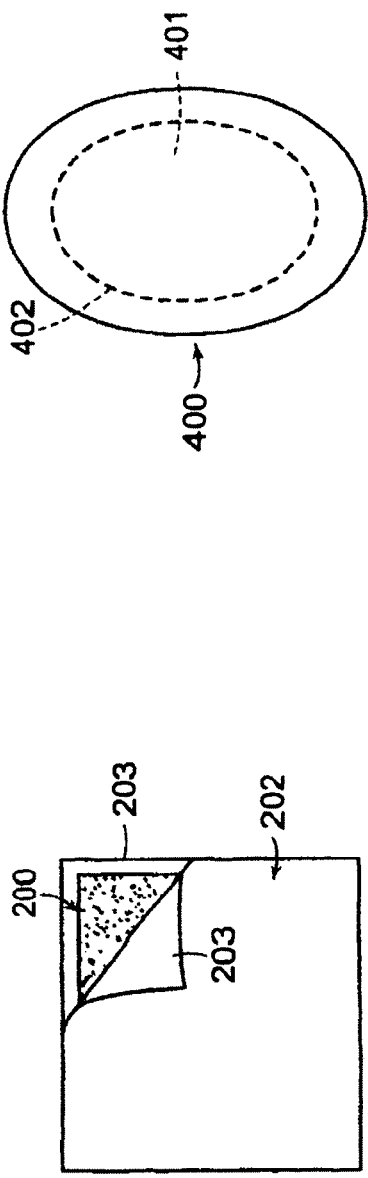
FIG. 16 is a front view of a package containing a body wipe carrying a copper ion treatment and showing the package partially open to remove the body wipe therefrom.

FIG. 15 illustrates an applicator 181 suitable for use in delivering a suppository 130 to the vagina or rectum. The applicator 181 is similar to the applicator 81 but does not have an internal thread at the forward end of the barrel 183. in addition, the plunger 185 of the applicator 181 has two internal flanges 193a and 193b within the barrel 183, the flange 193a controlling the distance that the plunger can be withdrawn relative to the barrel and the flange 193b serving to eject the suppository from the barrel when the plunger is depressed the full amount. In use, a suppository 130 is manually positioned in the open forward end of the barrel 183 as illustrated in FIG. 15. The open forward end of the barrel 183 is preferably sized to retain the suppository 130 in position without being overly snug or tight. The plunger 185 is withdrawn the full amount relative to the barrel 183, which coincides with abutment of internal flange 183a with the rearward end wall of the barrel 183. The forward end of the barrel 183 holding the suppository is then introduced in the vagina or rectal (anal) canal, and the applicator 181 is gently pushed into the vagina or rectal canal until the fingers holding the rearward end of the barrel 183 are adjacent or touch the entrance to the vagina or rectal canal. The finger flange 195 is then depressed to push the plunger 185 toward and into the barrel 183 as shown by the arrow in FIG. 15, thus causing the flange 193b to engage the suppository 130 and eject it from the forward end of the barrel into the vagina or rectal canal. The applicator 181 is then removed from the vagina or rectal canal, leaving the suppository in the vagina or rectal canal. The suppository will melt or dissolve in the vagina or rectal canal such that the copper ion treatment is released to contact anatomical tissue of the vagina or rectal canal and to mingle with body fluid present in the vagina or rectal canal. Another type of carrier that can be used to deliver the copper ion treatments to anatomical tissue is a body wipe. FIG. 16 illustrates a body wipe 200 contained in a sealed package 202 having front and rear walls 203. The body wipe 200 comprises a thin sheet of material disposed in a folded condition when retained between the front and rear walls 203, which are sealed along their peripheral edges. The body wipe 200 enclosed between the front and rear walls 203 contains a wet or moist copper ion treatment. The front and rear walls 203 may be grasped by the fingers at corresponding corners thereof and pulled in opposite directions similar to the pods 132 in order to separate the front and rear walls 203 and thereby allow the body wipe 200 to be removed from the package 202. FIG. 16 shows the package 202 in a partially open condition in which corresponding corner sections of the front and rear walls 203 have been peeled away from one another thereby providing access to the body wipe 200. Upon removal from the package 202, the body wipe 200 can be unfolded to its full size, which is substantially larger than its size in the folded condition, and can be used to wipe anatomical tissue to be treated causing the copper ion treatment to be transferred to the anatomical tissue. The body wipe 200 is advantageous for applying the copper ion treatments to the skin and the external genital and rectal areas.

Figure 17:
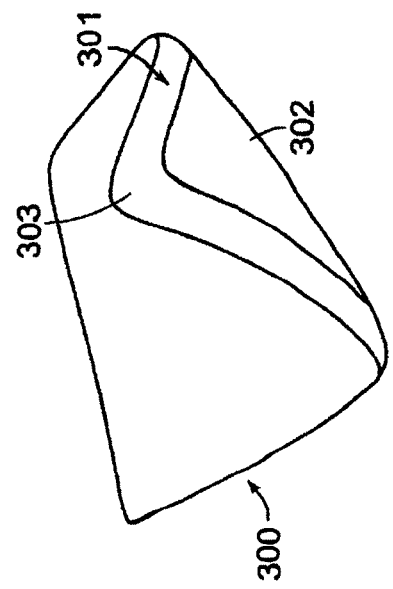
FIG. 17 is a perspective view of a wound dressing supplied with a copper ion treatment.

Another type of carrier for the copper ion treatments is a wound dressing, such as a band aid, gauze pad or similar device. Such earners can be selected from products that are commercially available for removable application to the skin to temporarily cover and protect an affected area of the skin. FIG. 17 depicts a carrier in the nature of a wound dressing 300 having a surface 301 for being placed in contact with the skin. The surface 301 includes a protective surface 302 for being positioned over a wound, and an adhesive border surrounding the surface 302. In use, a copper ion treatment, such as the copper ion-containing solution in original form, can be liberally sprayed onto the surface 302 of the carrier that is applied adjacent or in contact with the skin. Then, when the surface 302 of the carrier is applied adjacent or in contact with the skin and the carrier is left in place on the skin for a period of time, the copper ions contact or are transferred to the skin and provide the therapeutic effects described above. Of course, it would be possible to provide carriers of this type in sealed packages in which the carriers are pre-supplied or pre-treated with the copper ion treatment similar to the body wipe 200.

Figure 18:
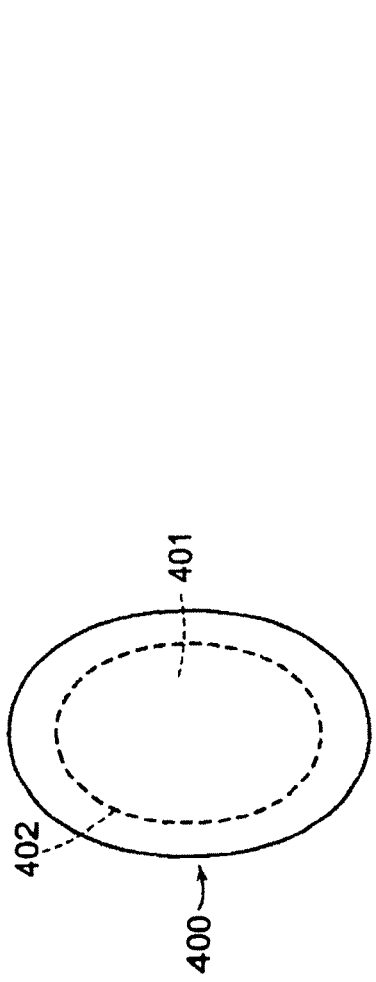
FIG. 18 is a plan view of a skin patch carrying a copper ion treatment.

A further type of carrier for the copper ion treatments is a skin patch, such as a dermal patch or a transdermal patch, represented at 400 in FIG. 18. The skin patch 400 has a drug delivery surface 401 containing the copper ion treatment surrounded by an adhesive border 402. The patch is applied to the skin and left in place for a period of time with the drug delivery surface in contact with the skin, causing the copper ions to diffuse through the skin where they can act locally or penetrate the capillaries for broader systemic effects. Examples of suitable transdermal patches are the transdermal and microneedle 3M Drug Delivery Systems manufactured by 3M Corporation.

Figure 19:
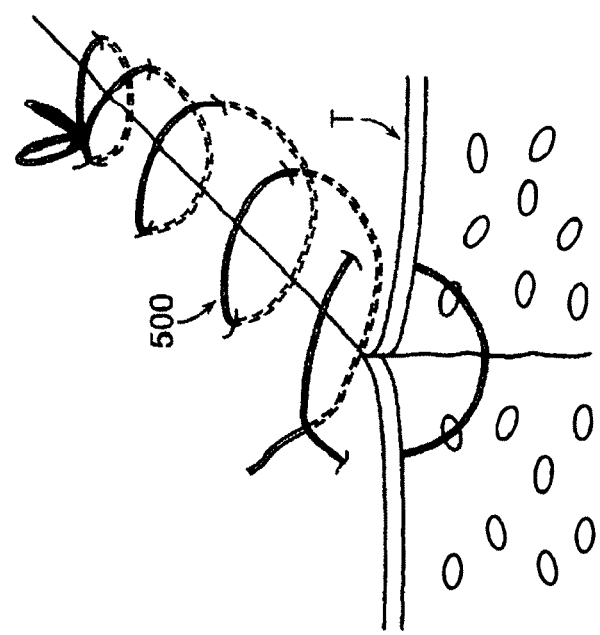
FIG. 19 is a perspective view of sutures created in anatomical tissue using suture material carrying a copper ion treatment.

An additional type of carrier for the copper ion treatments is suture material, represented at 500 in FIG. 19, used by medical professionals to close or suture external or internal incisions or wounds, i.e. "stitches." Prior to using the suture material 500, which can be conventional suture material, the suture material can be soaked in the copper ion-containing solution for a period of time in order to cover or saturate the suture material with the solution. Suture material can also be stored in sealed packages containing the copper ion-containing solution. Then, when the suture material 500 is used to create sutures or stitches in anatomical tissue T as seen in FIG. 19, the copper ions in the solution contact the anatomical tissue and provide the therapeutic effects previously described.

The copper ion-containing solution and the other forms of copper ion treatments described herein can be used on anatomical tissue in various areas of the body including the genital-rectal areas (vagina, vulva, penis, scrotum, rectum (anus), rectal (anal) canal and surrounding anatomical areas), the oral-respiratory-otic areas (mouth, throat, airway, nostrils and ears) and the dermatological areas (skin and nails) of the body. The treatment effects provided by the copper ion treatments encompass treatment of active or existing disease and other undesirable body conditions as well as the prevention of such diseases and conditions. The copper ion treatments are especially beneficial for their ability to kill or neutralize harmful or undesired pathogens and microbes including bacteria, viruses and fungi. Although the copper ion treatments are applied topically to anatomical tissue and have a localized effect on diseases and undesirable body conditions affecting the anatomical tissue, the copper ion treatments also have a broader systemic effect on diseases and undesirable body conditions. The effects realized with the copper ion treatments include antibacterial, antimicrobial, antiseptic, antifungal, antiviral, anti-pathogenic, anti-inflammatory, spermicidal, neutralization of free radicals, promotion of healing and tissue repair, prevention of biofilm, and immune-boosting effects. The diseases or conditions affecting the genital-rectal areas that are treatable with the copper ion treatments include vaginitis, bacterial vaginosis, hemorrhoids, vaginal dryness, imbalances in vaginal pH, bacterial infections caused by gonorrhea, chlamydia, *streptococcus* and *staphylococcus*, protozoan infections caused by trichomonas, pelvic inflammatory disease, viral infections caused by herpes (I and II), HPV and HIV, fungal infections caused by yeast, Candida, thrush and other fungi, exposure to sexually transmitted diseases, and the risk of undesired pregnancy (contraception). The diseases or conditions affecting the oral-respiratory-otic areas that are treatable with the copper ion treatments include bacterial infections caused by gonorrhea, chlamydia, *streptococcus* and *staphylococcus*, protozoan infections caused by trichomonas, viral infections caused by herpes (I and II), HPV and HIV, canker sores, mouth sores, mouth ulcers, colds, sinusitis, rhinosinusitis. sore throat, nasal discharge, congestion, runny nose, bronchitis, allergies, asthma, tonsillitis, wheezing, sneezing, ear infections, earache, pressure in the ears, cough, hoarseness, laryngitis, sore gums, periodontal disease, bad breath and tooth decay. The diseases or conditions affecting the dermatological areas that are treatable with the copper ion treatments include bacterial infections caused by *staphylococcus, streptococcus, enterobacter, e. coli* and pseudomonas, viral infections caused by shingles, herpes (I and II) and HPV, fungal infections such as athlete's foot, ringworm and toenail fungus, impetigo, rosacea, psoriasis, eczema, warts, sun/wind damage, dry skin, age spots, pigmentation, scarring, blisters, boils, cysts, pimples, cuts, scratches, burns, abrasions, splinters, insect bites and stings, animal bites and scratches, ulcers, loss of elasticity or collagen, wrinkles, sagging skin, acne, measles, chicken pox, and the presence of pathogens and microbes on the skin that is an inevitable consequence of daily life. Based on the result of laboratory testing, it is expected that the copper ion treatments will kill bacteria causing bacterial vaginosis, gonorrhea and chlamydia, and the viruses responsible for Herpes (I and II) and HIV at a kill rate of 99.99 percent in 6 hours. Accordingly, the copper ion treatments are sufficiently effective to "cure" the diseases and conditions described herein and to prevent the occurrence or development of such diseases and conditions. Similarly, copper has been demonstrated as having the capability to kill or render inactive *staphylococcus, streptococcus, enterobacter, trichomonas, E. coli* and *pseudomonas*. The copper ion treatments are highly effective at treating the various abnormal or undesired body conditions while being safe and non-toxic. In particular, copper toxicity is so rare that the World Health Organization (WHO) has determined that there is no need for setting an upper threshold for the ingestion of copper. The copper ion treatments can thus be safely used without concern for overdosing or improper use. Moreover, it is believed that, to date, no bacteria or other harmful microorganisms have been found to be capable of developing a resistance to copper, in contrast to the many bacteria and organisms that have developed or are in the process of developing resistance to conventional antibiotics. The multi-target effects of copper makes bacterial resistance extremely unlikely as copper kills bacteria very quickly and leaves almost no survivors. Consequently, there is neither the time for bacteria to "learn" how to resist the killing effect of copper or the possibility to pass on any knowledge to a significant population of survivors. The copper ion treatments provide a degree of efficacy and safety for treating a wide array of diseases and body conditions that far surpasses conventional pharmaceutical and non-pharmaceutical products and drugs available for treating the same conditions.

Figure 20:
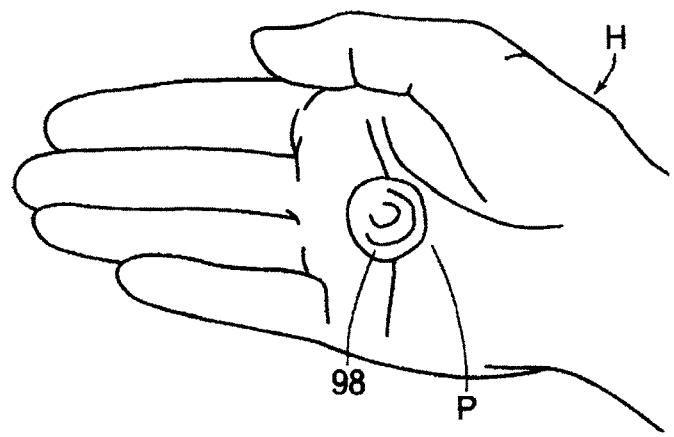
FIG. 20 is a broken top view of a dose of copper ion treatment in the form of lotion, cream, gel or foam dispensed onto the palm of a hand.
Figure 21:
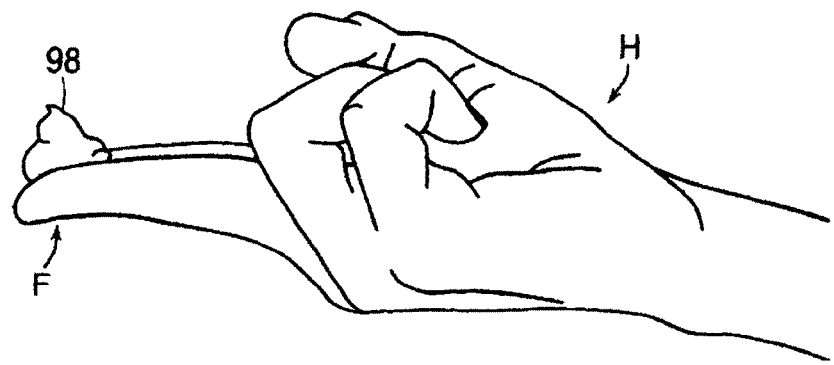
FIG. 21 is a broken side view of a dose of copper ion treatment in the form of lotion, cream gel or foam supported on the middle and index fingers of a hand used to apply the copper ion treatment to anatomical tissue.

When using a copper ion treatment on the skin or nails in the form of copper ion lotion, cream, gel or foam, the copper ion treatment will typically be topically applied to the skin or nails using one or more fingers of a hand as represented in FIGS. 20 and 21. FIG. 20 shows a dose of copper ion treatment 98 in the form of copper ion lotion, cream, gel or foam deposited on the palm P of a hand H. The dose is a dollop of copper ion lotion, cream, gel or foam in the approximate size of a nickel or quarter, but larger doses of copper ion treatment can be used in accordance with the size of the area on the skin to be treated. The dose can be delivered or deposited onto the palm P of the hand H from a device such as the devices 10, 50, 60 and 70 previously described above. The fingers F of the opposite hand may be used to "scoop" the dollop of copper ion treatment from the palm P, as seen in FIG. 21 which shows the dose of copper ion treatment 98 now deposited on the index and middle fingers F of the opposite hand H. Alternatively, the copper ion treatment can be dispensed or deposited directly onto one or more fingers F of the hand. Using one or more fingers F, the copper ion treatment 98 can be applied to anatomical tissue of the skin or nails and gently rubbed into the tissue.

According to an aspect of the invention, damaged or injured areas of the skin are treated by applying a topical copper ion treatment to the affected area of the skin as described below in Examples 33-37. The methods of Examples 33-37 are particularly advantageous for treating areas of the skin damaged or injured due to conditions including wounds, blisters, boils, warts, cysts, pimples, cuts, scratches, burns, sunburn, windburn, abrasions, splinters, foot and leg ulcers, insect bites or stings, animal bites or scratches, surgical incisions, and conditions creating breaks in the skin that provide an opportunity for the entry of pathogens and microbes. The methods of Examples 33-37 are particularly beneficial for treating active infection or inflammation in damaged or injured areas of the skin, for preventing or reducing the risk of infection or inflammation in damaged areas of the skin, promoting healing of damaged or injured areas of the skin and relieving discomfort or pain arising from damaged or injured areas of the skin. Examples 33, 34 and 35 describe methods that involve applying the copper ion-containing solution in original form to the skin. Examples 33, 34 and 35 utilize the copper ion-containing solution of Example 1, but the alternative copper ion-containing solutions of Examples 2-4 could be used. Example 33 is best carried out using the device 10 of FIG. 1 to spray the copper ion-containing solution on the skin. Example 34 can be carried out using the body wipe 200 of FIG. 16 or the swab 105 of FIG. 11. Example 35 is carried out using suture material 500 to apply the copper ion-containing solution, where the suture material 500 has been soaked in the copper ion-containing solution. Accordingly, the method of Example 35 applies to external or internal surgical incisions or wounds that require stitches or suturing.

Example 33

As soon as possible following damage or injury to an area of the skin, liberally spray the damaged or injured area of the skin with the copper ion-containing solution using several consecutive pumps of the spray pump nozzle 14. Allow the area of the skin to air dry. Repeat every four hours until the damaged or injured area of the skin has healed.

Example 34

As soon as possible following damage or injury to an area of the skin, gently wipe the damaged or injured area of the skin with the body wipe 200 carrying the copper ion-containing solution, or gently swab the damaged or injured area of the skin with the swab 105 carrying the copper ion-containing solution, to deposit a liberal amount of the copper ion-containing solution on the affected area of the skin. Allow the area of the skin to air dry. Repeat every four hours until the damaged or injured area of the skin has healed.

Example 35

In order to create stitches or sutures in open wounds or surgical incisions in anatomical tissue, stitch or suture the anatomical tissue using suture material that has been soaked or immersed in the copper ion-containing solution for 30 minutes.

The method of Example 36 involves applying a copper ion cream, gel, lotion or foam to the damaged or injured area of the skin, where the copper ion cream, gel, lotion or foam contains an amount of the copper ion-containing solution in the range of 5 percent to 30 percent of the total weight of the copper Son cream, gel, lotion or foam as described above in Examples 5-20, The method of Example 36 may be carried out using the device 50 to dispense the copper ion creams and gels, the device 60 to dispense the copper ion lotion, and the device 70 to dispense the copper ion foam. The copper ion cream, gel, lotion or foam can be dispensed from the corresponding device directly onto the affected area of skin but, more typically, the copper ion cream, gel, lotion or foam will be dispensed from the corresponding device onto the hand and applied to the affected area using one or more fingers as described above and illustrated in FIGS. 20 and 21.

Example 36

As soon as possible following damage or injury to an area of the skin, liberally apply a copper ion treatment in the form of copper ion cream, gel, lotion or foam to the damaged or injured area of the skin. Gently pat, rub or smooth the copper ion treatment into the affected area of the skin. Repeat every four hours until the damaged or injured area of the skin has healed.

When carrying out the methods of Examples 33, 34 and 36, and when carrying out the method of Example 35 to form external stitches or sutures, a protective wound dressing or pad can be placed over the affected area of the skin after the application of the copper ion treatment thereto. When using the method of Example 36 to treat foot or leg ulcers, the affected area of the leg or foot should be covered with gauze, which can be held in place using tape.

The method of Example 37 involves use of a wound dressing to deliver or apply the copper ion treatment to the damaged or injured area of the skin. In particular, Example 37 employs a wound dressing 300 having a protective surface 301 to be placed in contact with or adjacent the damaged or injured area of the skin, in which the surface 301 has been supplied with copper ion treatment, such as the copper ion-containing solution, as previously described above. The wound dressing 300 would be held or secured in place on the skin by means of the adhesive border 302.

Example 37

As soon as possible following damage or injury to an area of the skin, position a protective surface of a wound dressing that has been supplied with a copper ion treatment over the damaged or injured area of the skin with the surface adjacent or in contact with the damaged or injured area of the skin. Secure the wound dressing in place on the skin and allow the wound dressing to remain in place for four hours. Remove the wound dressing from the skin after it has been allowed to remain in place on the skin for four hours, and repeat the method using a new wound dressing supplied with the copper ion treatment. Continue to repeat every four hours until the damaged or injured area of the skin has healed.

The method of Example 37 can be modified to use the skin patch 400 in place of the wound dressing, and normally the skin patch would be placed on healthy, undamaged skin and would be left in place on the skin for a considerably longer period of time. As a result of the copper tons from the copper ion treatment contacting the anatomical tissue in the methods of Examples 33-37, the local and systemic therapeutic effects as previously described above are realized.

Another aspect of the invention involves treating rashes on the skin using a copper ion treatment as explained below in Examples 38-40. The methods of Examples 38-40 are particularly advantageous for treating rashes arising from conditions including one or more of eczema, psoriasis, rosacea, acne, impetigo, chicken pox, measles, shingles, ringworm and herpes. The method of Example 38 utilizes the copper ion-containing solution of Example 1; however, the copper ion-containing solutions of Examples 2-4 could be utilized. The method of Example 38 can be carried out using the device 10 of FIG. 1 to spray the copper ion-containing solution on the affected area of the skin. The method of Example 39 may be carried out using the body wipe 200 of FIG. 16.

Example 38

As soon as possible following diagnosis or the onset of a rash on the skin, liberally spray the area of the rash on the skin with the copper ion-containing solution using several consecutive pumps of the spray pump nozzle 14. Allow the area of the skin to air dry. Repeat every four hours until the rash has disappeared.

Example 39

As soon as possible following diagnosis or the onset of a rash on the skin, wipe the area of the rash on the skin with the body wipe 200 carrying the copper ion-containing solution to deposit a liberal amount of the copper ion-containing solution on the rash. Allow the area of the skin to air dry. Repeat every four hours until the rash has disappeared.

The method of Example 40 involves applying a copper ion treatment in the form of a copper Ion cream, gel, lotion or foam to a rash on the skin, where the copper ion cream, gel, lotion or foam contains an amount of the copper ion-containing solution in the range of 5 percent to 30 percent of the total weight of the copper ion cream, gel lotion or foam. The method of Example 40 may be carried out using the device 50 to dispense the copper ion creams and gels, the device 60 to dispense the copper ion lotion, and the device 70 to dispense the copper ion foam. The copper ion cream, gel, lotion or foam can be dispensed from the corresponding device directly onto the area of the rash but, more typically, the copper ion cream, get, lotion or foam will be dispensed from the corresponding device onto the hand and applied to the area of the rash using the fingers and hand as pointed out above.

Example 40

As soon as possible following diagnosis or the onset of a rash on the skin, liberally apply the copper ion treatment in the form of copper ion cream, gel, lotion or foam to the area of the rash on the skin. Gently pat, rub or smooth the copper ion treatment into the area of the rash on the skin. Repeat every four hours until the rash has disappeared.

An additional aspect of the invention pertains to treating cold sores or fever blisters on the skin, and particularly cold sores or fever blisters on the lips. Example 41 describes a method for treating cold sores (fever blisters) using a copper ion treatment in the form of copper ion cream, lotion or gel containing an amount of the copper ion-containing solution in the range of 5 percent to 30 percent by weight of the total weight of the copper ion cream, lotion or gel. In carrying out the method of Example 41, the copper ion cream, lotion or gel will be deposited onto the tip of a finger which is then used to apply the copper ion cream, lotion or gel to the cold sore. The method of Example 41 is beneficial for treating cold sores caused by the herpes virus (I and II) on account of the anti-viral effects that result from the copper ions coming into contact with the anatomical tissue affected by the cold sore.

Example 41

As soon as possible following the first symptom of a cold sore, apply a liberal amount of copper ion treatment in the form of copper ion cream, lotion or gel to the cold sore. Gently pat rub or smooth the copper ion treatment into the cold sore. Repeat every four hours until the cold sore has disappeared.

It is also an aspect of the invention to use the copper ion treatments as cosmetic treatments on the skin as represented by the method of Example 42. According to this aspect of the invention, the therapeutic effects provided when the copper ions in the copper ion treatment contact the skin result in improved appearance of skin affected by wrinkles, sagging skin, undesirable pigmentation, age spots, dry skin, loss of collagen and loss of skin tone. The method of Example 42 may best be carried out using the fingers to apply to the skin a copper ion treatment in the form of a copper ion cream or lotion. Also, copper ion gels could be used, particularly gels of thin consistency in the form of serums. The copper ion cream, lotion or gel contains an amount of the copper ion-containing solution in the range of 5 percent to 30 percent of the total weight of the copper Ion cream, lotion or gel.

Example 42

Apply a liberal amount of a copper ion treatment in the form of copper ion cream, lotion or gel to the skin on the face. Gently rub, pat or smooth the copper ion treatment into the skin. Repeat the application of the copper ion treatment such that the copper ion treatment is applied to the facial skin two times each day on a daily basis.

The method of Example 42 can be modified to include application of the copper ion treatment to the skin on the neck. The method of Example 42 can be carried out by applying the copper ion treatment to the skin once in the morning and once in the evening every day on a regular basis. Preferably, the copper ion treatment should be applied to clean, dry skin for maximum effectiveness.

An additional aspect of the invention is represented by Example 43, which pertains to a method of treating "athlete's foot", a common infection that appears on the feet. The method of Example 43 may best be carried out using the fingers and one or more hands to apply to an affected foot a copper ion treatment in the form of a copper ion cream or lotion containing an amount of the copper ion-containing solution in the range of 5 percent to 30 percent of the total weight of the copper ion cream or lotion.

Example 43

As soon as possible following diagnosis or the first symptoms of athlete's foot, apply a liberal amount of a copper ion treatment in the form of copper ion cream or lotion to the affected area of the foot. Rub the copper ion treatment into the affected area. Apply the copper ion treatment to the opposite foot in the same manner if the opposite foot is also affected by athlete's foot. Repeat the application of the copper ion treatment to the one or both affected feet such that the copper ion treatment is applied twice a day to the one or both affected feet and is continued every day until the athlete's foot is resolved.

It is preferred that the method of Example 43 be carried out by applying the copper ion treatment to the one or both affected feet in the morning and in the evening each day. In addition, it is helpful if a clean white sock is worn on the one or both affected feet following the application of the copper ion treatment in the morning.

The copper ion treatments can also be used to sanitize areas of the skin, particularly the hands. The antiseptic, antibacterial, antiviral, antifungal, anti-pathogenic, antimicrobial and anti-inflammatory effects realized as a result of the copper ions contacting the skin when the copper ion treatments are applied thereto make the copper ion treatments particularly well-suited for use as skin and hand sanitizers. Example 44 describes a method of sanitizing an area of the skin using a copper ion treatment in the form of the copper ion-containing solution or in the form of copper ion lotion, gel or foam containing an amount of the copper ion-containing solution in the range of 6 percent to 30 percent of the total weight of the copper ion lotion, gel or foam. The method of Example 44 can be carried out by spraying the copper ion-containing solution on the area of the skin to be sanitized, dispensing the copper ion lotion, gel or foam directly on the skin or on the fingers or hand which are then used to apply the copper ion lotion, gel or foam to the area of the skin to be sanitized, or by using the body wipe 200 to apply the copper ion-containing solution to the skin.

Example 44

Apply a copper ion treatment in the form of a copper ion-containing solution, a copper ion lotion, a copper ion gel or a copper ion foam to the area of the skin to be sanitized. Gently rub or spread the copper ion treatment on the area of the skin. Allow the area of the skin to air dry. Repeat the process as desired to sanitize the area of the skin.

A further aspect of the invention involves treating nail fungus using the copper ion treatments as represented by the method set forth in Example 45. The method of Example 45 may best be carried out using a copper ion cream containing an amount of copper ion-containing solution in the range of 5 percent to 30 percent of the total weight of the copper ion cream. However, it should be appreciated that other forms of the copper ion treatment could be used. When using a copper ion cream to carry out the method of Example 45. the cream will normally be applied by hand to a nail affected by a fungal condition and the fingers of the hand will be used to rub the cream into and around the affected nail. Depending on the form of copper ion treatment used, however, it should be appreciated that the copper ion treatment could be applied to the affected nail using the brush 45 of the device 40 depicted in FIG. 4 or the swab 105 of the device 101 depicted in FIG. 11, for example.

Example 45

As soon as possible following the first sign of a fungal condition in a toenail or fingernail, apply a liberal amount of a copper ion treatment in the form of a copper ion cream to the affected nail. Using the fingers, thoroughly rub the copper ion cream into and around the affected nail. Repeat the application such that the copper ion treatment is applied to the affected nail twice a day for each day until the nail fungus has disappeared.

The copper ion treatments can be used on the skin or nails as a treatment for active or existing infections, diseases, inflammation or undesired body conditions or as a treatment to prevent the development of infections, diseases, inflammation and undesired body conditions. The diseases or conditions affecting the dermatological areas that are treatable with the copper ion treatments include one or more of bacterial infections caused by *staphylococcus, streptococcus, enterobacter, E. coli* and *pseudomonas*, viral infections caused by shingles, herpes (I and II) and HPV, fungal infections such as athlete's foot, ringworm and fungus affecting the toenails or fingernails, impetigo, rosacea, psoriasis, eczema, warts, sunburn, windburn, dry skin, age spots, pigmentation, scarring, blisters, boils, cysts, pimples, cuts, scratches, incisions, burns, abrasions, splinters, insect bites and stings, animal bites and scratches, ulcers, particularly ulcers of the legs and feet, loss of elasticity or collagen, wrinkles, sagging skin, acne, measles, chicken pox, and the presence of pathogens and microbes on the skin.

Inasmuch as the present invention is subject to many variations, modifications and changes in detail it is intended that all subject matter discussed above or shown in the accompanying drawings be interpreted as illustrative only and not be taken in a limiting sense.

The invention claimed is:

1. A method of treating a bacterial infection caused by gonorrhea, the method comprising administering a copper ion suspension to a subject in need thereof, wherein the copper ion suspension consists of:
   copper ions;
   a saline solution; and
   one or more buffers;
   wherein the copper ions are leached into a first solution from a solid copper metal by:
   (a) placing the solid copper metal in the first solution consisting of the saline solution and the one or more buffers;
   (b) allowing the solid copper metal to remain in the first solution for a predetermined period of time, during which predetermined period of time the solid copper metal leaches into the first solution; and
   (c) removing the solid copper metal from the first solution after the predetermined period of time.

2. The method of claim 1, wherein the bacterial infection caused by gonorrhea affects anatomical tissue of the subject in need thereof, and wherein the copper ion suspension is applied such that the copper ions of the copper ion suspension contact the anatomical tissue affected by the bacterial infection caused by gonorrhea.

3. The method of claim 1, wherein the method comprises preventing of biofilm formation caused by the bacterial infection caused by gonorrhea.

4. The method of claim 1, wherein the copper ion suspension is disposed in a second solution, a cream, a lotion, a gel, a foam, a paste, a spray, or a suppository.

5. The method of claim 4, wherein the cream, gel, lotion, paste, spray, or suppository contains an amount of the copper ion suspension in the range of 5 percent to 30 percent of the total weight of the second solution, the cream, the lotion, the gel, the foam, the paste, the spray, or the suppository.

6. The method of claim 1, wherein the solid copper metal consists of a pure copper.

7. The method of claim 1, wherein the solid copper metal consists of a copper alloy.

8. The method of claim 7, wherein the copper alloy is selected from the group consisting of a brass, a bronze, a copper-nickel alloy, and a copper-zinc alloy.

9. A method of treating a bacterial infection caused by gonorrhea, the method comprising:
(a) making a copper ion suspension, wherein making the copper ion suspension comprises the steps of:
(i) placing a solid copper metal in a solution comprising saline and a buffer;
(ii) allowing the solid copper metal to remain in the solution for a predetermined period of time, during which predetermined period of time the solid copper metal leaches into the solution; and
(iii) removing the solid copper metal from the solution after the predetermined period of time;
wherein the copper ion suspension comprises:
copper ions, and
the solution comprising saline and the buffer, and
(b) administering the copper ion suspension.

10. The method of claim 9, wherein the bacterial infection caused by gonorrhea affects anatomical tissue of the subject in need thereof, and wherein the copper ion suspension is applied such that the copper ions of the copper ion suspension contact the anatomical tissue affected by the bacterial infection caused by gonorrhea.

11. The method of claim 9, wherein the method comprises preventing of biofilm formation caused by the bacterial infection caused by gonorrhea.

12. The method of claim 9, wherein the copper ion suspension is disposed in a second solution, a cream, a lotion, a gel, a foam, a paste, a spray, or a suppository.

13. The method of claim 12, wherein the cream, gel, lotion, paste, spray, or suppository contains an amount of the copper ion suspension in the range of 5 percent to 30 percent of the total weight of the second solution, the cream, the lotion, the gel, the foam, the paste, the spray, or the suppository.

14. The method of claim 9, wherein the solid copper metal consists of a pure copper.

15. The method of claim 9, wherein the solid copper metal consists of a copper alloy.

16. The method of claim 15, wherein the copper alloy is selected from the group consisting of a brass, a bronze, a copper-nickel alloy, and a copper-zinc alloy.

* * * * *